United States Patent
Kealey et al.

(10) Patent No.: US 11,154,410 B2
(45) Date of Patent: Oct. 26, 2021

(54) SPIRAL-BASED THIN-FILM MESH SYSTEMS AND RELATED METHODS

(71) Applicant: Monarch Biosciences, Inc., Los Angeles, CA (US)

(72) Inventors: Colin Kealey, Los Angeles, CA (US); Vikas Gupta, Los Angeles, CA (US)

(73) Assignee: Monarch Biosciences, Inc., Los Angeles, CA (US)

(*) Notice: Subject to any disclaimer, the term of this patent is extended or adjusted under 35 U.S.C. 154(b) by 318 days.

(21) Appl. No.: 16/024,649

(22) Filed: Jun. 29, 2018

(65) Prior Publication Data

US 2020/0000612 A1    Jan. 2, 2020

(51) Int. Cl.
*A61F 2/90* (2013.01)
*C23C 30/00* (2006.01)

(52) U.S. Cl.
CPC .......... *A61F 2/90* (2013.01); *C23C 30/00* (2013.01); *A61F 2210/0014* (2013.01); *A61F 2210/0076* (2013.01); *A61F 2230/0091* (2013.01); *A61F 2240/001* (2013.01); *A61F 2250/0067* (2013.01)

(58) Field of Classification Search
CPC ...... A61F 2/82; A61F 2/90; A61F 2/91; A61F 2/0063; A61F 2230/0091
See application file for complete search history.

(56) References Cited

U.S. PATENT DOCUMENTS

| | | | |
|---|---|---|---|
| 5,876,432 A | 3/1999 | Lau et al. | |
| 7,220,275 B2* | 5/2007 | Davidson | A61F 2/82 623/1.35 |
| 7,842,081 B2* | 11/2010 | Yadin | A61F 2/856 623/1.35 |
| 9,060,836 B2* | 6/2015 | Jagger | A61F 2/0063 |
| 2002/0010507 A1 | 1/2002 | Ehr et al. | |
| 2004/0244853 A1* | 12/2004 | Harman | F15D 1/04 137/808 |
| 2008/0288050 A1 | 11/2008 | Addonizio et al. | |
| 2009/0276029 A1 | 11/2009 | Caro et al. | |
| 2012/0016461 A1 | 1/2012 | Harman | |
| 2013/0230601 A1* | 9/2013 | Itskovitz-Eldor | A61K 35/12 424/572 |
| 2017/0173262 A1* | 6/2017 | Veltz | A61B 5/0022 |

OTHER PUBLICATIONS

PCT International Search Report, PCT/US2019/39999, dated Nov. 6, 2019, 14 pages.

* cited by examiner

*Primary Examiner* — Jason-Dennis N Stewart
(74) *Attorney, Agent, or Firm* — Haynes and Boone, LLP

(57) ABSTRACT

A spiral-based thin-film mesh for medical devices and related methods is provided. The spiral-based thin-film mesh may be used as a stent cover for a stent device. The thin-film mesh may include a plurality of spirals. The spirals allow the thin-film mesh to expand omni-directionally. In one or more embodiments, the spirals may be logarithmic spirals, golden spirals, approximated golden spirals, box Phi spirals, or Fibonacci spirals. The thin-film mesh may be formed from thin-film Nitinol (TFN), and may be fabricated via sputter deposition on a micropatterned wafer.

17 Claims, 29 Drawing Sheets

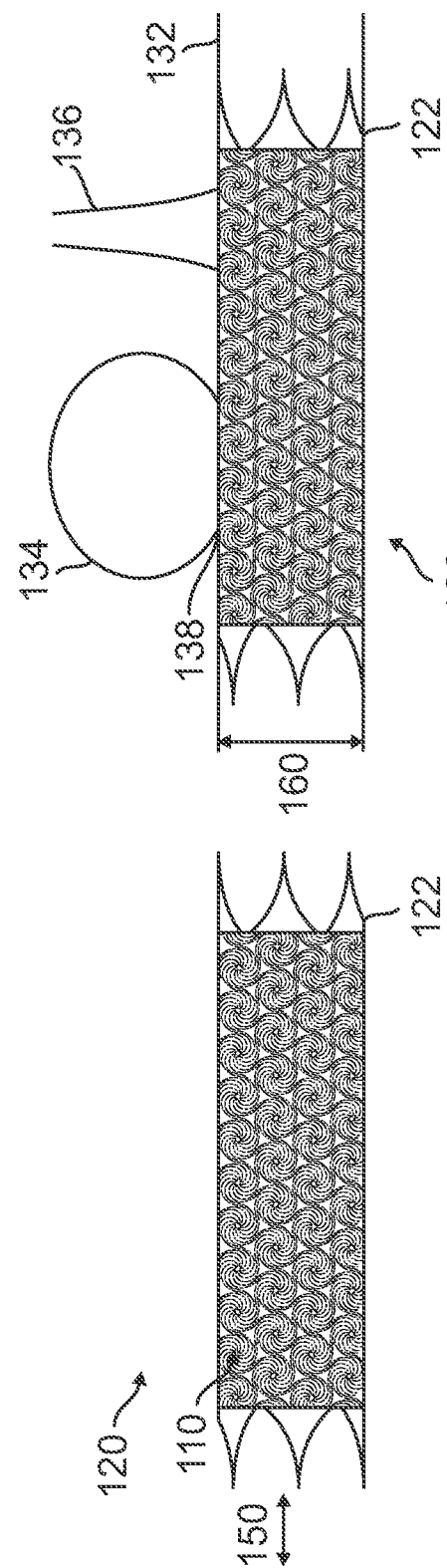

4 box Phi spiral

3 Box Equilateral Triangle (3 arm) Based System

4 Box Equilateral Triangle (3 arm) Based System

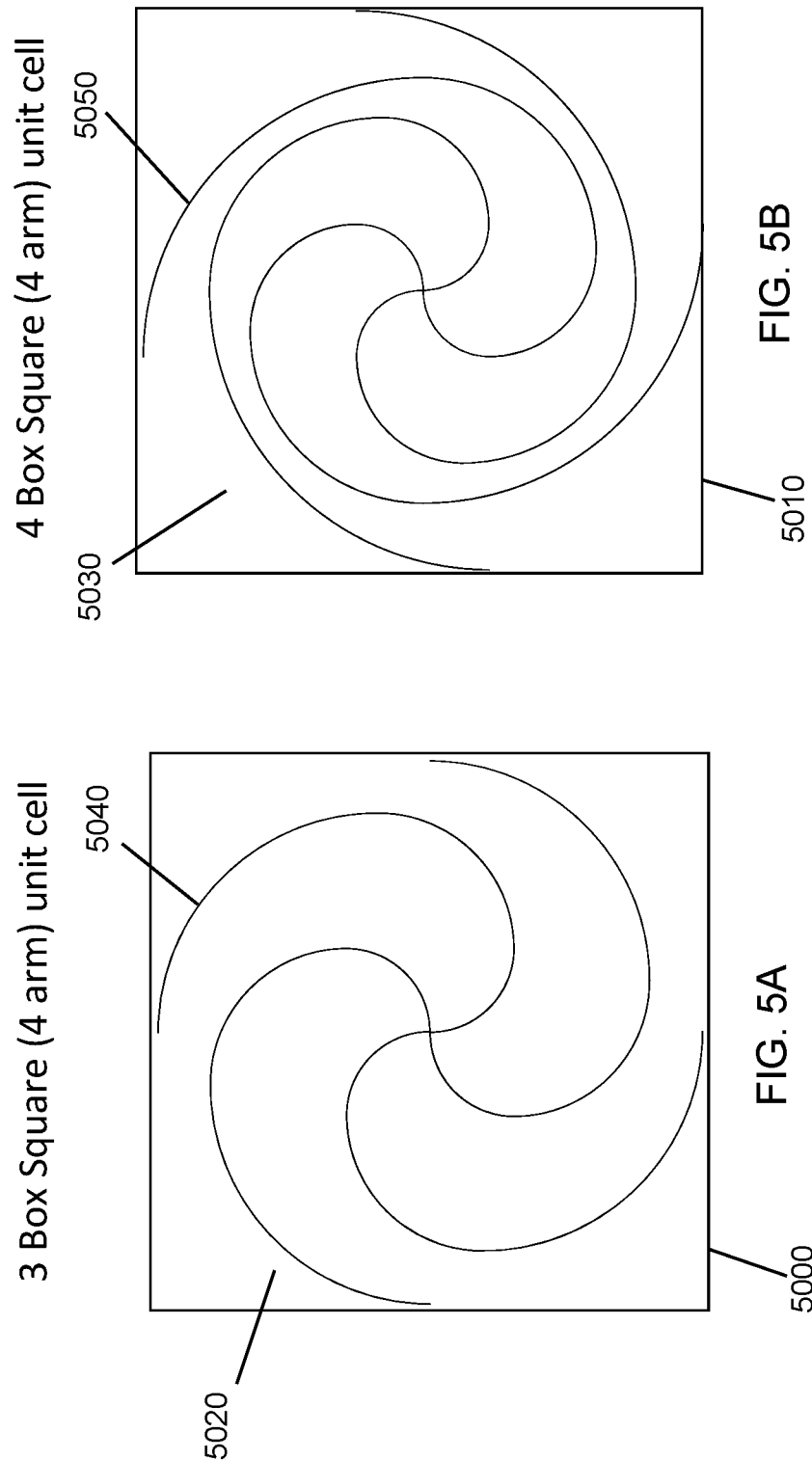

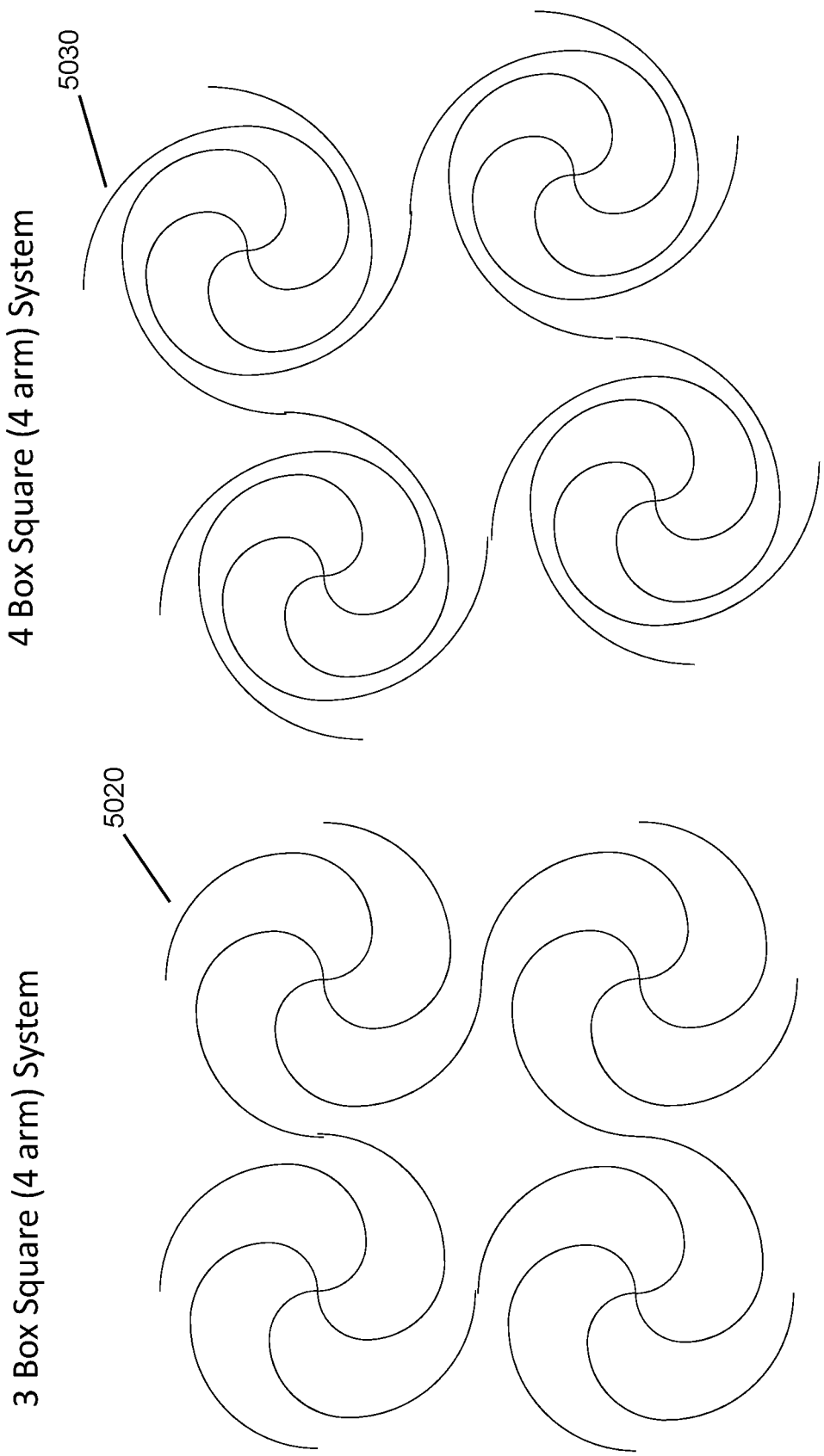

3 Box Dodecagon (12 arm) System

3 Box Dodecagon (12 arm) System
Triangular interconnects added

3 Box Dodecagon (12 arm) System
Alternative tessellation for 12 arm system

4 Box Dodecagon (12 arm) System

4 Box Dodecagon (12 arm) System
Triangular interconnects added

Dodecagon (12 arm) System at theoretical full expansion

2 Box icositetragon (24 arm) unit cell

Tessellated icositetragon (24 arm) system

12 Arm Spiral - no triangular interconnects
Before Stretch

12 Arm Spiral - no triangular interconnects
After Stretch

12 Arm Spiral - with alternative triangular interconnects

12 Arm Spiral - with alternative triangular interconnects

SPIRAL-BASED THIN-FILM MESH SYSTEMS AND RELATED METHODS

TECHNICAL FIELD

The present disclosure generally relates to medical devices and, more particularly, to spiral-based thin-film mesh systems and related methods.

BACKGROUND

Medical implants must typically conform to a wide variety of irregular anatomic surfaces. For example, a conventional endovascular stent typically is a braided-wire device or laser-cut device that is compressed and delivered using a catheter and guidewire to a treatment location inside a patient. Stents are used to treat a wide variety of clinical pathologies including atherosclerotic arterial and aneurysmal disease.

A thin-film mesh may be used to cover the endovascular stent. The stent may be deployed in tortuous vascular beds, and may under undergo dramatic changes in the radial and axial dimensions during the delivery and implantation process. Accordingly, there is a need in the art for an improved thin-film mesh that allows for flexibility in multiple dimensions.

SUMMARY

The present disclosure relates to a method, system, and apparatus for a spiral-based thin-film mesh. The thin-film mesh is flexible in multiple dimensions and can therefore easily conform to irregular anatomic surfaces. These properties make the thin-film mesh an ideal component of implantable medical devices. An additional advantage of the thin-film mesh is that it can be used to locally deliver therapeutic modalities of all types including, but not limited to, small molecules, peptides, proteins, antibodies, polymers, and cells to any anatomic site of interest.

In one or more embodiments, a thin-film mesh device comprises a thin-film mesh that comprises a plurality of spirals that are omni-directionally expandable. In at least one embodiment, the plurality of spirals is arranged around an approximate central point on the thin-film mesh. In some embodiments, each of the spirals comprises three spiral arms, four spiral arms, six spiral arms, twelve spiral arms, or twenty-four spiral arms. In at least one embodiment, for each of the spirals, the distance between adjacent spiral arms increases as the spiral arms radiate out from the center of the spiral. In one or more embodiments, the thin-film mesh further comprises a plurality of triangular interconnects, where each of the triangular interconnects connects three of the spirals with one another.

In one or more embodiments, each of the spirals is a logarithmic spiral, a golden spiral, an approximated golden spiral, a box Phi spiral, or a Fibonacci spiral. In some embodiments, the box Phi spiral is a two box Phi spiral, a three box Phi spiral, or a four box Phi spiral. In at least one embodiment, the thin-film mesh comprises thin-film Nitinol (TFN).

In one or more embodiments, the thin-film mesh is coated and/or conjugated to a therapeutic modality. In some embodiments, the therapeutic modality comprises small molecules, peptides, antibodies, polymers, biopolymers, cell, and/or engineered cells.

In one or more embodiments, a thin-film mesh device comprises a backbone extending in a longitudinal axis, and a thin-film mesh assembled on the backbone. In one or more embodiments, the thin-film mesh comprises a plurality of spirals that are omni-directionally expandable.

In one or more embodiments, the thin-film mesh comprises a cylindrical shape, where at least one of the spirals is expanded such that the thin-film mesh expands along the longitudinal axis of the cylindrical shape and along a circumferential direction of the cylindrical shape. In some embodiments, the thin-film mesh is expandable along the circumferential direction allowing the cylindrical shape to expand radially increasing a diameter of the cylindrical shape. In one or more embodiments, the thin-film mesh comprises thin-film Nitinol (TFN). In some embodiments, the backbone comprises a plurality of S-shaped curves.

In at least one embodiment, the thin-film mesh is coated or treated with a therapeutic modality prior to implant. The therapeutic modality may be comprised of small molecules, proteins, antibodies, polymers, and/or cells.

In one or more embodiments, a method for forming a thin-film mesh comprises deep reactive ion etching a micropattern of trenches on a surface of a substrate, the trenches corresponding to negative areas of a plurality of spirals in the thin-film mesh to be formed. The method further comprises depositing a lift-off layer on the etched substrate. Also, the method comprises depositing a first Nitinol layer over the lift-off layer. Further, the method comprises etching the lift-off layer to form the thin-film mesh.

In one or more embodiments, the trenches further correspond to negative areas of triangular interconnects, which each connect three of the spirals with one another.

In one or more embodiments, the method further comprises depositing a bonding layer on at least one area of the first Nitinol layer. Also, the method comprises depositing a sacrificial layer on a remaining area of the first Nitinol layer. In addition, the method comprises depositing a second Nitinol layer on the bonding layer and the sacrificial layer. Further, the method comprises annealing the first Nitinol layer and the second Nitinol layer with the bonding layer. In one or more embodiments, the etching further etches the sacrificial layer to form the thin-film mesh having a three dimensional shape.

In one or more embodiments, a stent comprises a backbone extending in a longitudinal axis, and a stent cover assembled on the backbone. In one or more embodiments, the stent cover comprises a thin-film mesh, which comprises a plurality of spirals that are omni-directionally expandable. In some embodiments, the thin-film mesh further comprises a plurality of triangular interconnects, where each of the triangular interconnects connects three of the spirals with one another.

The features, functions, and advantages can be achieved independently in various embodiments of the present disclosure or may be combined in yet other embodiments.

BRIEF DESCRIPTION OF THE DRAWINGS

FIG. 1A is a diagrammatic perspective side view of a thin-film mesh device according to an embodiment.

FIG. 1B is a diagrammatic cross-sectional view of a blood vessel with an aneurysm in which a thin-film mesh device is placed according to an embodiment.

FIG. 2A illustrates a three box Phi spiral according to an embodiment.

FIG. 2B illustrates a four box Phi spiral according to an embodiment.

FIG. 3A illustrates a three box Phi spiral, equilateral triangle-shaped unit cell comprising a spiral having three spiral arms according to an embodiment.

FIG. 3B illustrates a four box Phi spiral, equilateral triangle-shaped unit cell comprising a spiral having three spiral arms according to an embodiment.

FIGS. 5A and 5B show two different types of box Phi spiral, square-shaped unit cells according to embodiments.

FIG. 5A illustrates a three box Phi spiral, square-shaped unit cell comprising a spiral with four spiral arms according to an embodiment.

FIG. 5B illustrates a four box Phi spiral, square-shaped unit cell comprising a spiral with four spiral arms according to an embodiment.

FIG. 6A illustrates an exemplary three box Phi spiral, square-based system comprising a plurality of interconnected spirals of FIG. 5A according to an embodiment.

FIG. 6B illustrates an exemplary four box Phi spiral, square-based system comprising a plurality of interconnected spirals of FIG. 5B according to an embodiment.

FIG. 7A illustrates a three box Phi spiral, hexagon-shaped unit cell comprising a spiral having six spiral arms according to an embodiment.

FIG. 7B illustrates a four box Phi spiral, hexagon-shaped unit cell comprising a spiral having six spiral arms according to an embodiment.

FIG. 9A illustrates a three box Phi spiral, dodecagon-shaped unit cell comprising a spiral having twelve spiral arms according to an embodiment.

FIG. 9B illustrates a four box Phi spiral, dodecagon-shaped unit cell comprising a spiral having twelve spiral arms according to an embodiment.

Figure 1C:
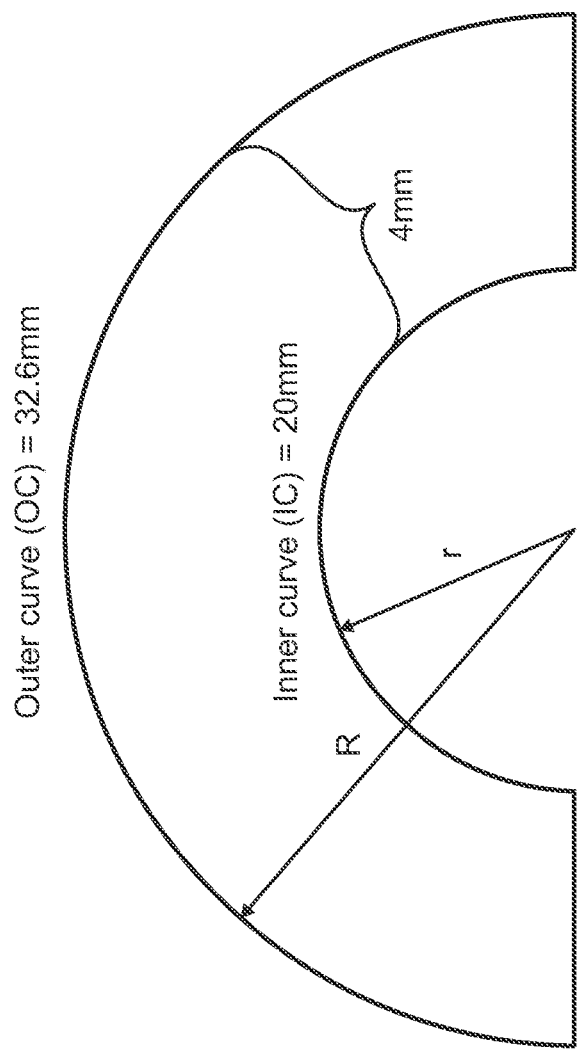
FIG. 1C illustrates a scenario in which a thin-film micromesh device is contoured or bent according to an embodiment.

Embodiments of the present disclosure and their advantages are best understood by referring to the detailed description that follows. It should be appreciated that like reference numerals are used to identify like elements illustrated in one or more of the figures, in which the showings therein are for purposes of illustrating the embodiments and not for purposes of limiting them.

DETAILED DESCRIPTION

In the following description, numerous details are set forth in order to provide a more thorough description of the system. It will be apparent, however, to one skilled in the art, that the disclosed system may be practiced without these specific details. In the other instances, well known features have not been described in detail, so as not to unnecessarily obscure the system.

Embodiments of the present disclosure may be described herein in terms of functional components and various processing steps. Those skilled in the art will appreciate that embodiments of the present disclosure may be practiced in conjunction with other components, and that the systems described herein are merely example embodiments of the present disclosure.

I. Spiral-Based Thin-Film Mesh

The methods and apparatus disclosed herein provide an operative system for a spiral-based thin-film mesh. In one or more embodiments, the system of the present disclosure provides a spiral-based thin film mesh that may be utilized for various different medical applications.

As previously mentioned above, there is a need for thin-film meshes that allow for flexibility in multiple dimensions. As such, the thin-film meshes need to be flexible and capable of stretching in any direction. In addition, for medical device applications, the thin-film meshes need to be capable of being efficiently "packed" to maintain a desired pore size, percent metal coverage, and pore-density per unit area. The thin-film meshes also need to be able to (1) undergo extreme deformities while maintaining structural integrity such that they are able to be delivered via minimally invasive means (e.g., by catheters, laparoscopes, thoracoscopes, and/or needles), (2) conform precisely to a medical devices support structure (e.g., a stent, as it is deployed in tortuous anatomy), (3) maintain pore sizes where the largest strut-to-strut distance is sufficient to block flow (e.g., for a diverting stent, and/or to encourage tissue in-growth and reconstruction of anatomic defects, where the mesh serves as a scaffold for cell growth), and (4) be used as a delivery platform for small molecules, proteins, antibodies, polymers, cells, and cell-based therapeutics because of its advantageous pore size, surface area to volume ratio, and strut dimensions. The disclosed spiral-based thin-film meshes are able to meet these desired criteria.

The spiral-based thin-film mesh of the present disclosure comprises a plurality of spirals. The spirals may be of various different types of spirals including, but not limited to, logarithmic spirals, golden spirals, approximated golden spirals, box Phi spirals, or Fibonacci spirals. In addition, the spirals may comprise various different numbers of spiral arms and may be connected with one another by various different means (e.g., via triangular interconnects) and arrangements. Examples of various different types of spirals, along with various different connections and arrangements of the spirals, that may be employed for the disclosed thin-film mesh will be discussed below and are depicted in FIGS. 2A-17B.

The spirals of the thin-film mesh allow for the thin-film mesh to be omni-directionally expandable (i.e. expandable in all directions). The thin-film mesh may be employed as a standalone device, or as a covering or key component of a medical implant (e.g., a stent cover) of a cylindrical-shaped thin-film mesh device, such as an endovascular stent (e.g., refer to FIGS. 1A, 1B, and 18). The thin-film mesh is capable of expanding in multiple directions, such as in radial directions and longitudinal directions of the cylindrical-shaped thin-film mesh device. The ability of the thin-film mesh to expand flexibly in multiple dimensions allows for the thin-film mesh device to expand wholly within irregularly-shaped blood vessels such that the thin-film mesh lines the inner surface of the irregularly-shaped blood vessels. The thin-film mesh may otherwise be included in other types of medical devices, such as a thin-film mesh scaffold for tissue engineering or for local delivery of therapy modalities of all types, for its advantageous properties as further described herein.

A particular advantage of spiral-based thin-film meshes having spirals is that they are: (1) completely closed-cell, meaning that there are no unattached corners of the unit cells, (2) capable of expanding in any direction, (3) extremely efficient at packing a large amount of material (e.g., mesh) into a small space, and (4) are "self-similar", meaning that they have the same degree of curvature at all points on the spiral, thereby making them well suited to stretching because the stress is distributed evenly throughout the spiral arm as it is straightened. These properties are particularly advantageous for thin-film meshes being used in medical applications because medical implants must conform to tortuous anatomy, and must therefore be capable of expanding and contracting on multiple axes.

Another advantage of the spiral-based thin-film mesh design is that it maintains a very high pore density and a low strut-to-strut distance, even when stretched to its fullest capacity. This is particularly advantageous for applications where the goal is to reconstruct an anatomic defect, and/or to deliver a high concentration of small molecules, a high concentration of large molecules, cell therapy, biopolymers, or polymers conjugated or otherwise attached to the mesh. Thus, the spiral-based thin-film meshes have a wide applicability in medicine due to their low profile, high pore density per unit surface area, ability to stretch in any direction, ability to be combined with other therapeutic modalities, and their ease of incorporation into minimally-invasive medical devices and other implants. The use of spirals (e.g., logarithmic spirals) in a thin-film mesh, allows for the thin-film mesh to have the particularly advantageous properties of omni-directional stretch capabilities, tunable pore size of the fenestrations of the thin-film mesh, and tunable percent metal coverage of the thin-film mesh.

As used herein, the thin-film mesh may be less than 100 μm (micrometers or microns) in thickness. In various embodiments, the thin-film mesh may be formed using fenestrated thin-film Nitinol (TFN). Other thin-film mesh materials may be used to form the thin-film mesh disclosed herein. The following discussion is thus directed to TFN meshes without loss of generality.

II. Spiral-Based Thin-Film Mesh Device

As previously mentioned above, the disclosed thin-film mesh is flexible in multiple dimensions and can therefore easily conform to irregular anatomic surfaces. As such, these properties make the thin-film mesh an ideal component of various different implantable medical devices. One such implantable device is an endovascular stent.

FIG. 1A is a diagrammatic perspective side view of thin-film mesh device 120 (e.g., an endovascular stent) that includes a thin-film mesh 110 and a backbone 122 (e.g., a stent backbone). Thin-film mesh 110 expanded to its three-dimensional form (e.g., a cylindrical tube or other shape)

may be assembled over backbone 122, which provides structural support for thin-film mesh 110 while maintaining the advantageous features of thin-film mesh 110, such as fibrin deposition and cell growth (e.g., endothelialization) when placed in a blood vessel.

The thin-film mesh 110 comprises a plurality of interconnected spirals, and is cylindrical in shape. The spirals allow for the thin-film mesh 110 to be omni-directionally expandable. At least one of the spirals of the thin-film mesh 110 may be expanded such that the thin-film mesh 110 expands along the longitudinal axis of the cylindrical shape and along the circumferential direction of the cylindrical shape. The thin-film mesh 110 may be expandable along the circumferential direction, thereby allowing the cylindrical shape to expand radially such that the diameter of the cylindrical shape increases.

FIG. 1B shows a diagrammatic cross-sectional view of a blood vessel 132 with an aneurysm 134 and a branch vessel 136 (e.g., a branch artery) in which thin-film mesh device 120 of FIG. 1A is implanted. Thin-film mesh device 120 may advantageously be used as a flow diverter due to the properties of thin-film mesh 110. Flow diverters may be required to strike a balance between diverting flow from an aneurysm sac, while permitting flow in any perianeurysmal branch vessels. Thin-film mesh 110 advantageously diverts blood flow into aneurysm 134 and promotes rapid deposition of fibrin and endothelialization at a neck 138 of aneurysm 134 so that aneurysm 134 is occluded, while at the same time allowing blood flow through branch vessel 136.

Thin-film mesh device 120 advantageously has a reduced rate of delayed aneurysm rupture when compared to conventional flow diverters. Conventional wire flow-diverter stents may provide occlusion of aneurysm necks, but because the pores of such devices are often filled with particles made up of blood coagulation products, inflammatory cells, and cellular debris, such particles may be dislodged and cause delayed aneurysm rupture. Indeed, endothelialization is slow to occur and is often partial at best in conventional wire flow-diverter stents. In contrast, thin-film mesh 110 provides a structure on which the blood vessel walls are rapidly rebuilt through endothelialization, promoting a healthy and stable cellular lining, and because the cellular lining is not prone to dislodging as particles of blood coagulation products and the like, the rate of delayed aneurysm rupture is significantly reduced.

FIG. 1C illustrates a scenario in which the cylindrical-shaped thin-film device 120 is contoured or bent into a U-shape. The U-shape may be required to conform to a particular treatment location in a patient. The inner radius r of the U-shape may be about 6.37 millimeter (mm), the outer radius R of the U-shape may be about 10.37 mm, and the diameter of the cylindrical-shaped thin film device 120 may be about 4 mm. In such scenario, the outer curve (about 32.6 mm) may be about 63% longer than the inner curve (about 20 mm). To conform to such treatment location, the outer-curve side of the cylindrical-shaped thin-film device 120 would have to expand about 63% more than the inner-curve side along the longitudinal direction 150 of the cylindrical-shaped thin-film device 120. Thus, a conventional cylindrical-shaped thin-film device 120 that expands mainly in the radial directions and has limited expandability or flexibility in the longitudinal direction may not meet such requirements.

Accordingly, an improved thin-film mesh 110 that allows for flexibility in multiple dimensions is proposed. For example, the improved thin-film mesh 110 may comprise a plurality of interconnected spirals. In particular, the spirals of the thin-film mesh 110 allow for the thin-film mesh to flexibly expand both in the radial directions and along the longitudinal axis of the cylindrical-shaped thin-film device 120. In addition, the thin-film mesh 110 may bend or contour during the delivery process and conform to various shapes of treatment locations in patients.

III. Spiral Designs for Spiral-Based Thin-Film Mesh

The thin-film mesh 110 is structured such that is comprises a plurality of tessellated unit cells. Each of the unit cells comprises a spiral, which may be a logarithmic spiral. FIGS. 2A-17B illustrate a variety of various different spirals that may be employed for the unit cells of the disclosed thin-film mesh 110. The unit cells are arranged around an approximate central point on the thin-film mesh 110. The unit cells may be scaled and tessellated into two dimensions to create structures with unique and desirable properties. Additional structural modifications may be made by increasing or decreasing the number of unit cells arranged around the central point, and/or by increasing the length of the spiral arms of each of the spirals of the unit cells.

In geometry, it is known that only three shapes tessellate perfectly in two dimensions: the equilateral triangle, the square, and the hexagon. Thus, thin-film meshes 110 comprising unit cells composed of spirals comprising three spiral arms (which forms an equilateral triangle-shaped unit cell, refer to FIGS. 3A and 3B), four spiral arms (which forms a square-shaped unit cell, refer to FIGS. 5A and 5B), or six spiral arms (which forms a hexagon-shaped unit cell, refer to FIGS. 7A and 7B) tessellate perfectly, and are particularly efficient embodiments of this design. While the thin-film meshes may be manufactured from tessellating unit cells with spirals having almost any number of spiral arms, these three unit cell shapes (i.e. equilateral triangle (which comprises a spiral comprising three spiral arms), square (which comprises a spiral comprising four spiral arms), and hexagon (which comprises a spiral comprising six spiral arms)) provide the most basic arrangement, where no additional structures are needed to connect the tessellated unit cells.

The thin-film mesh 110 may comprise a plurality of spirals, which may be logarithmic spirals. Logarithmic spirals have a polar equation of $r=ae^{b\theta}$, where r is equal to the distance from the origin, $\theta$ is equal to the angle from the x-axis, and a and b are arbitrary constants. Logarithmic spirals are "self-similar", meaning that they have the same shape regardless of their size.

A golden spiral and a Fibonacci spiral are special cases of the logarithmic spiral. The thin-film mesh 110 may comprise a plurality of golden spirals or Fibonacci spirals. A golden spiral is a logarithmic spiral whose growth factor is Phi ($\phi$), the golden ratio (i.e. 1.68). The Greek letter Phi ($\phi$) is used to represent the golden ratio. The golden spiral gets wider (or further from the origin) by a factor of $\phi$ for every quarter turn the spiral makes. A golden spiral with an initial radius equal to one has a polar equation of $r=\phi^{\theta(2/\pi)}$. The polar equation of the golden spiral is $r=ae^{b\theta}$, where the absolute value of b is equal to 0.0053468 for $\theta$ in degrees.

Similar spirals to the golden spiral are often referred to as approximate golden spirals. The thin-film mesh 110 may comprise a plurality of approximated golden spirals. These spirals approximate a golden spiral, however are often not a true logarithmic spiral. For example, an approximate golden spiral may be formed by first starting with a rectangle for which the ratio between its length and width is the golden ratio. This rectangle is then partitioned into a square and a similar rectangle, and the rectangle is then split the same way. After continuing this process for an arbitrary number of steps, the result will be an almost complete partitioning of the rectangle into squares. The corners of the squares are connected by quarter-circles to form the approximate golden spiral.

Another example of an approximate golden spiral is a Fibonacci spiral. A Fibonacci spiral is constructed by starting with a rectangle partitioned into two squares. In each step, a square the length of the rectangle's longest side is added to the rectangle. Since the ratio between consecutive Fibonacci numbers approaches the golden ratio as the Fibonacci numbers approach infinity, the shape of the Fibonacci spiral becomes more similar to the shape of the golden spiral as more squares are added.

It should be noted that logarithmic spirals are known to be an efficient means of distributing material around a central core. For example, in nature, sunflowers distribute their seeds in a Phi ($\phi$) spiral pattern. This arrangement ensures efficient packing of seeds and equal access to sunlight.

Figure 2A:
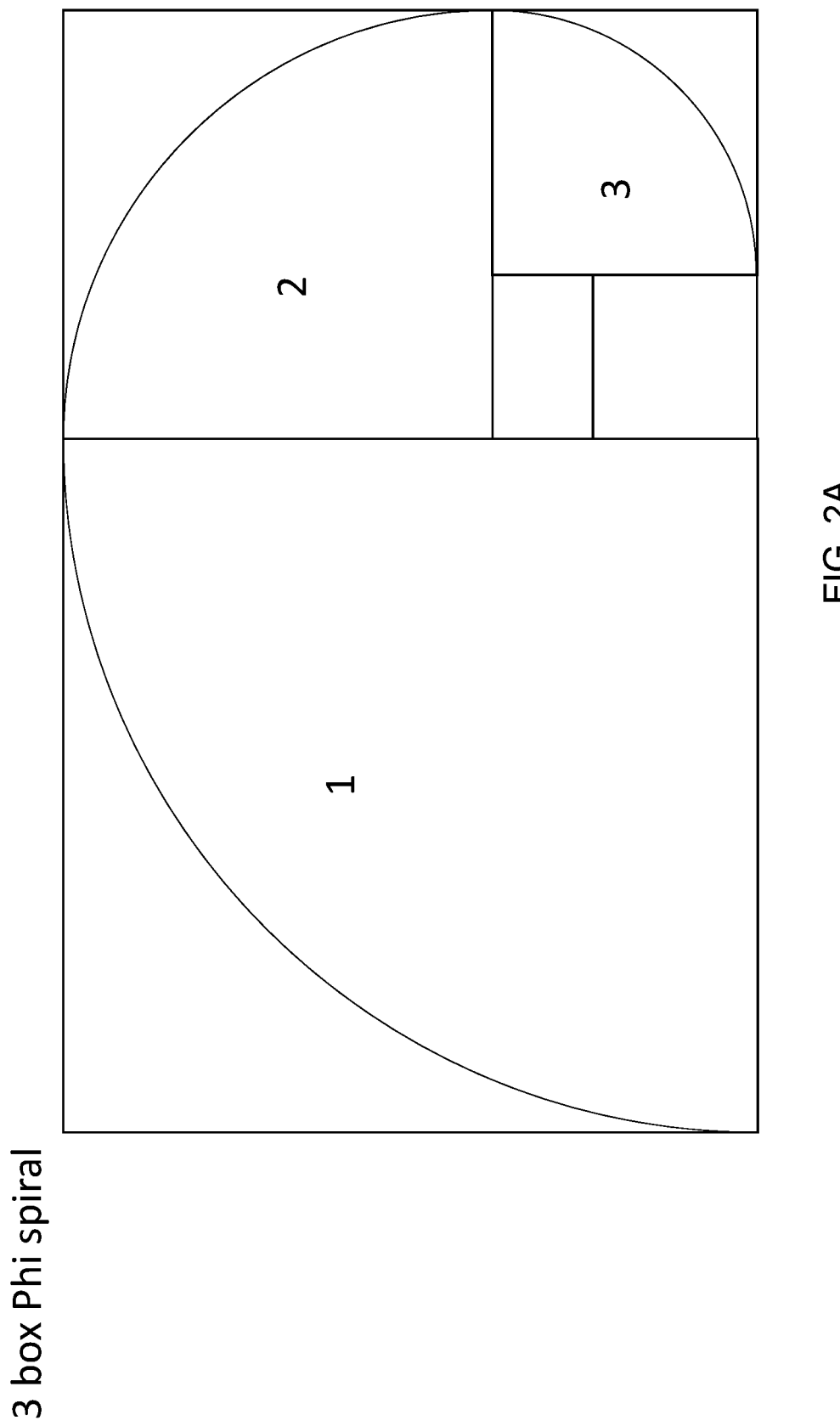
FIGS. 2A and 2B show two different types of box Phi spirals according to embodiments.
Figure 2B:
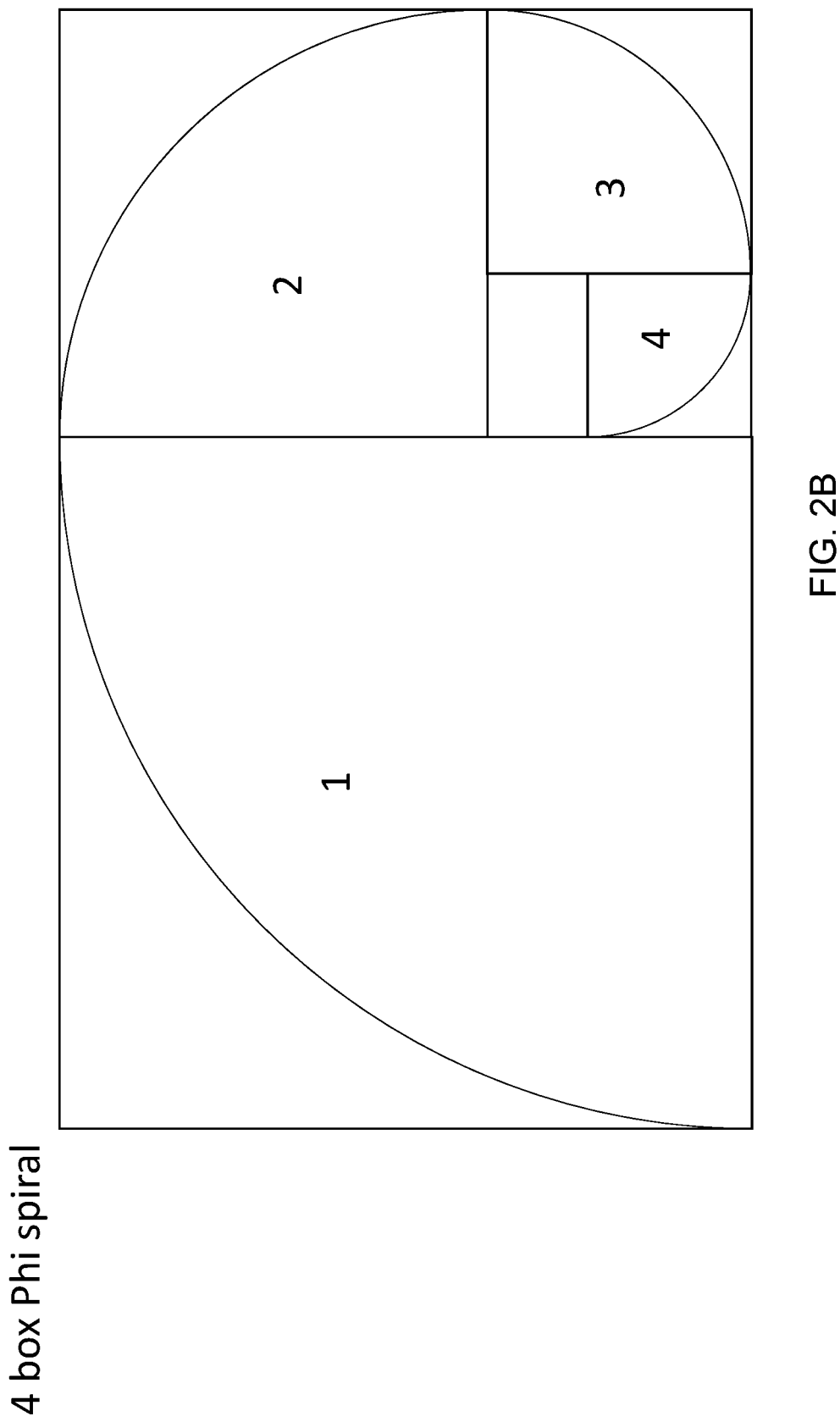
Figure 13:
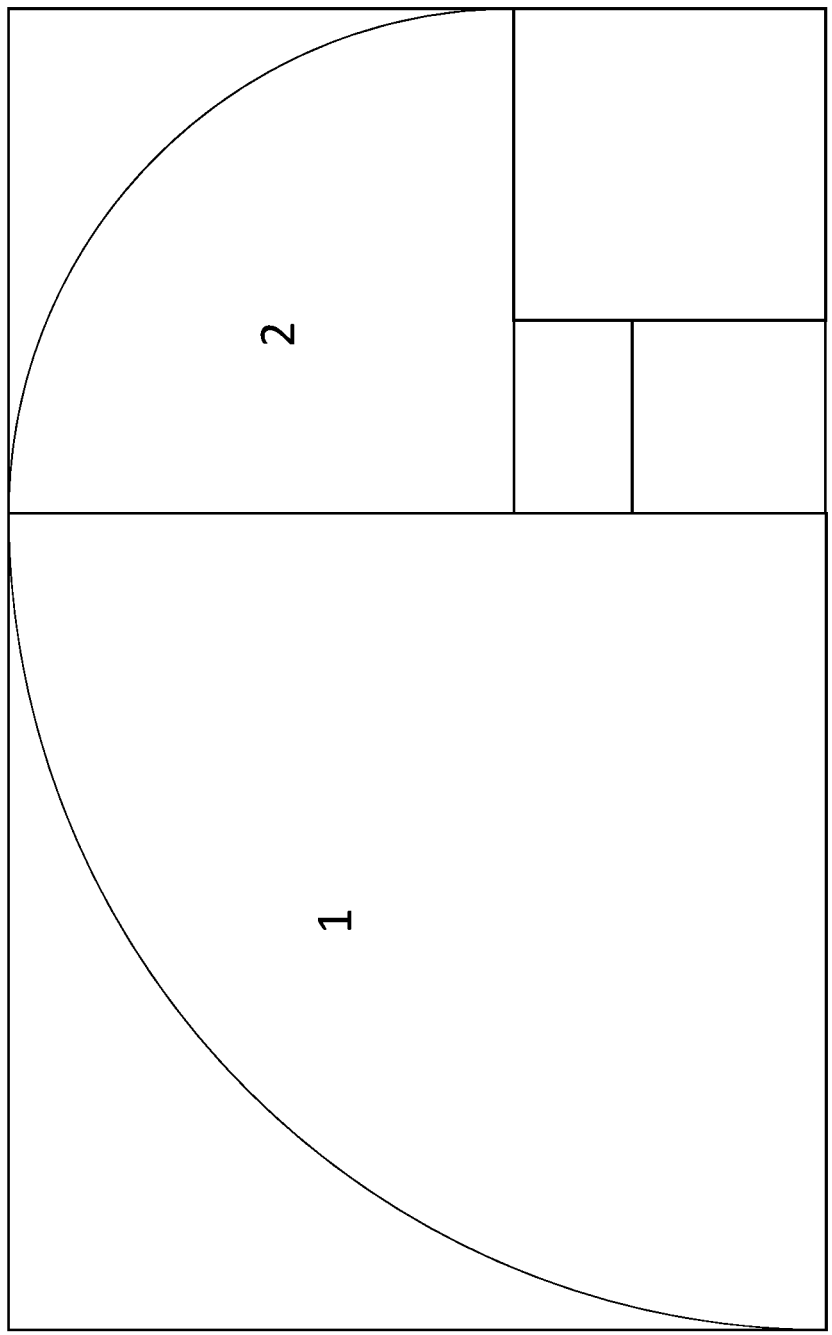
FIG. 13 illustrates a two box Phi spiral according to an embodiment.

The unit cells of the thin-film mesh 110 may be of a variety of different unit cell shapes including, but not limited to, an equilateral triangle-shaped unit cell (comprising a spiral with three spiral arms), a square-shaped unit cell (comprising a spiral with four spiral arms), a hexagon-shaped unit cell (comprising a spiral with six spiral arms), a dodecagon-shaped unit cell (comprising a spiral with twelve spiral arms), and a icositetragon-shaped unit cell (comprising a spiral with twenty-four spiral arms). Each of the unit cells may comprise a spiral. The spirals of the unit cells may be box Phi ($\phi$) spirals. FIGS. 2A, 2B, and 13 show different box Phi spirals that may be employed for the spirals of the unit cells of the thin-film mesh 110. Specifically, FIG. 2A illustrates a three box Phi spiral, FIG. 2B illustrates a four box Phi spiral, and FIG. 13 illustrates a two box Phi spiral.

Figure 3B:
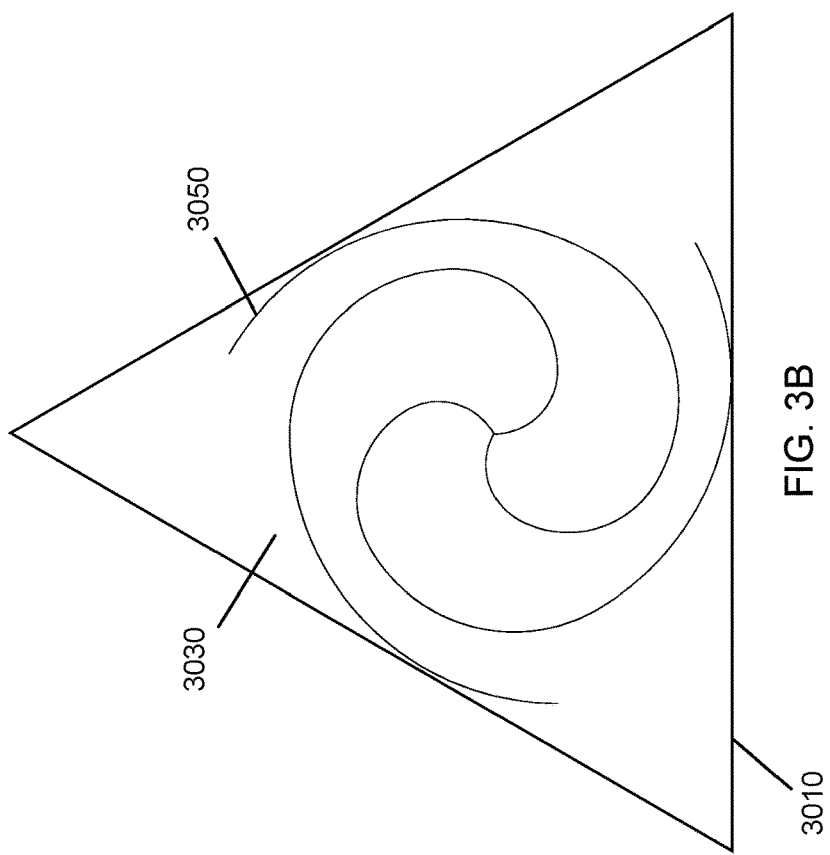
FIGS. 3A and 3B show two different types of box Phi spiral, equilateral triangle-shaped unit cells according to embodiments.
Figure 3A:
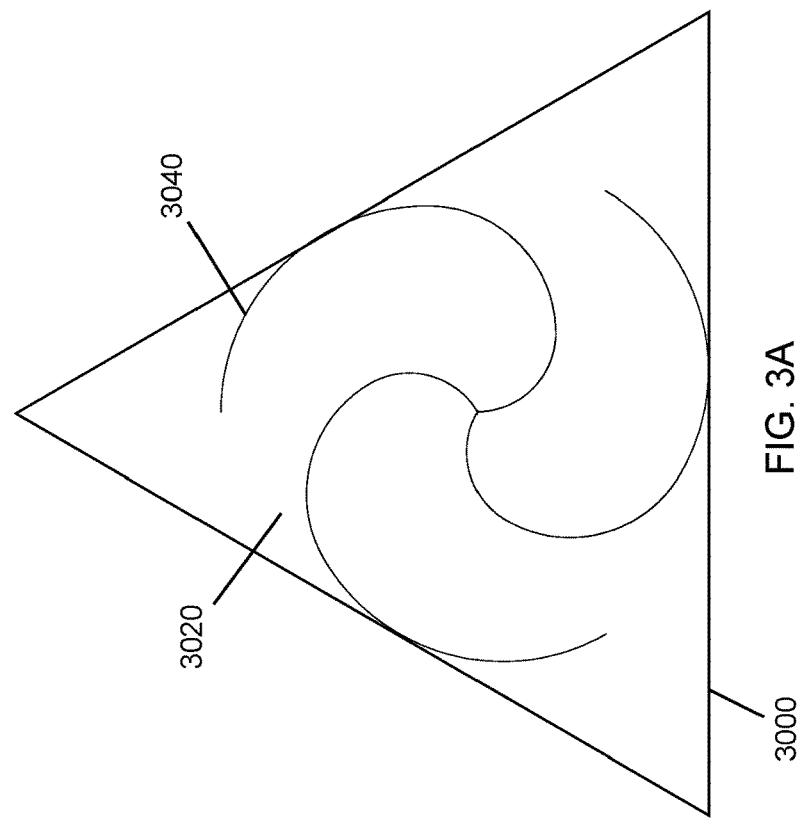
Figure 4A:
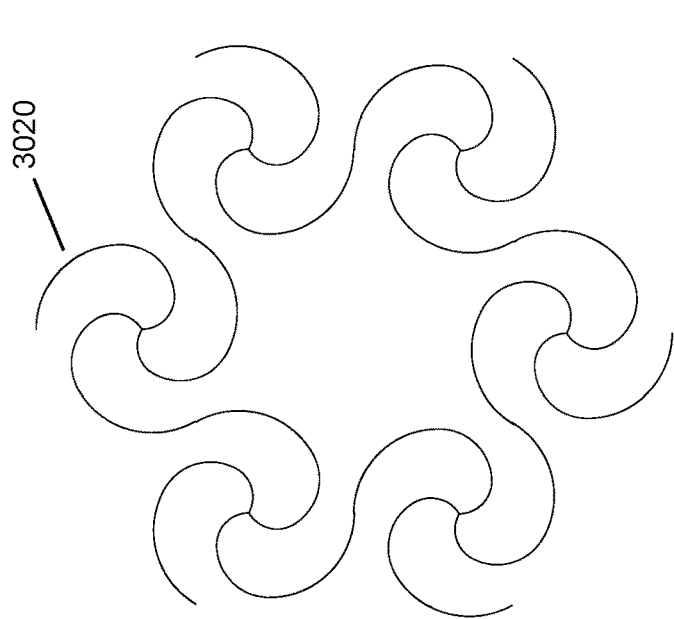
FIG. 4A illustrates an exemplary three box Phi spiral, equilateral triangle-based system comprising a plurality of interconnected spirals of FIG. 3A according to an embodiment.
Figure 4B:
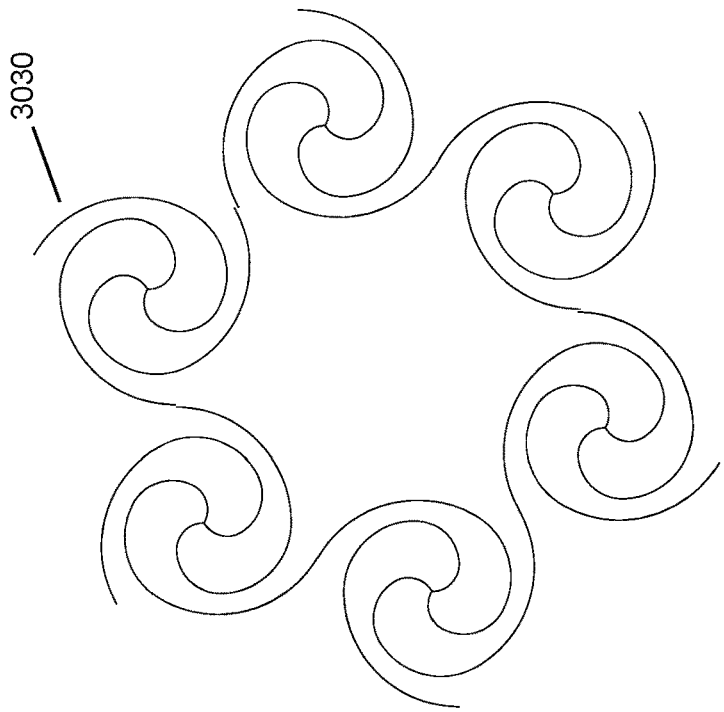
FIG. 4B illustrates an exemplary four box Phi spiral, equilateral triangle-based system comprising a plurality of interconnected spirals of FIG. 3B according to an embodiment.

The various different types of unit cells that may be employed by the thin-film mesh 110 may comprise various different types of box Phi spirals. Referring to the figures, FIGS. 3A and 3B depict an exemplary three box Phi spiral, equilateral triangle-shaped unit cell 3000 and an exemplary four box Phi spiral, equilateral triangle-shaped unit cell 3010, respectively; where the equilateral triangle-shaped unit cells 3000, 3010 of FIGS. 3A and 3B each comprise a spiral 3020, 3030 having three spiral arms 3040, 3050. FIG. 4A shows an exemplary three box Phi spiral, equilateral triangle-based system comprising a plurality of interconnected spirals 3020 of three box Phi spiral, equilateral triangle-shaped unit cells 3000; and FIG. 4B shows an exemplary four box Phi spiral, equilateral triangle-based system comprising a plurality of interconnected spirals 3030 of four box Phi spiral, equilateral triangle-shaped unit cells 3010. Although the systems depicted in FIGS. 4A and 4B each show a total of six unit cells 3000, 3010, the thin-film mesh 110 may comprise more or less unit cells 3000, 3010 than is shown in FIGS. 4A and 4B.

FIGS. 5A and 5B depict an exemplary three box Phi spiral, square-shaped unit cell 5000 and an exemplary four box Phi spiral, square-shaped unit cell 5010, respectively; where the square-shaped unit cells 5000, 5010 of FIGS. 5A and 5B each comprise a spiral 5020, 5030 having four spiral arms 5040, 5050. FIG. 6A shows an exemplary three box Phi spiral, square-based system comprising a plurality of interconnected spirals 5020 of three box Phi spiral, square-shaped unit cells 5000; and FIG. 6B shows an exemplary four box Phi spiral, square-based system comprising a plurality of interconnected spirals 5030 of four box Phi spiral, square-shaped unit cells 5010. The thin-film mesh 110 may comprise more or less unit cells 5000, 5010 than the four unit cells 5000, 5010 as is shown in the systems depicted in FIGS. 6A and 6B.

Figure 7B:
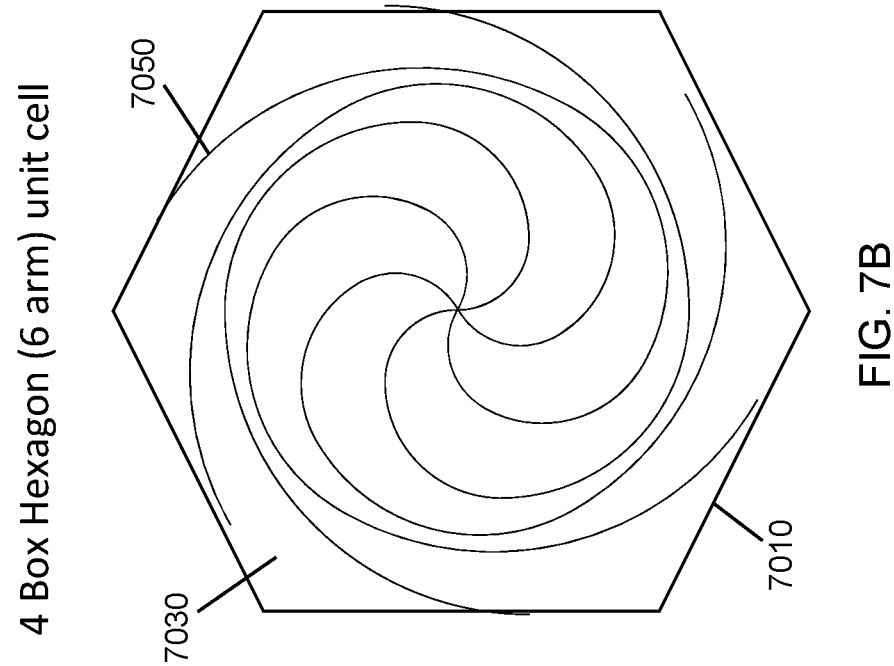
FIGS. 7A and 7B show two different types of box Phi spiral, hexagon-shaped unit cells according to embodiments.
Figure 7A:
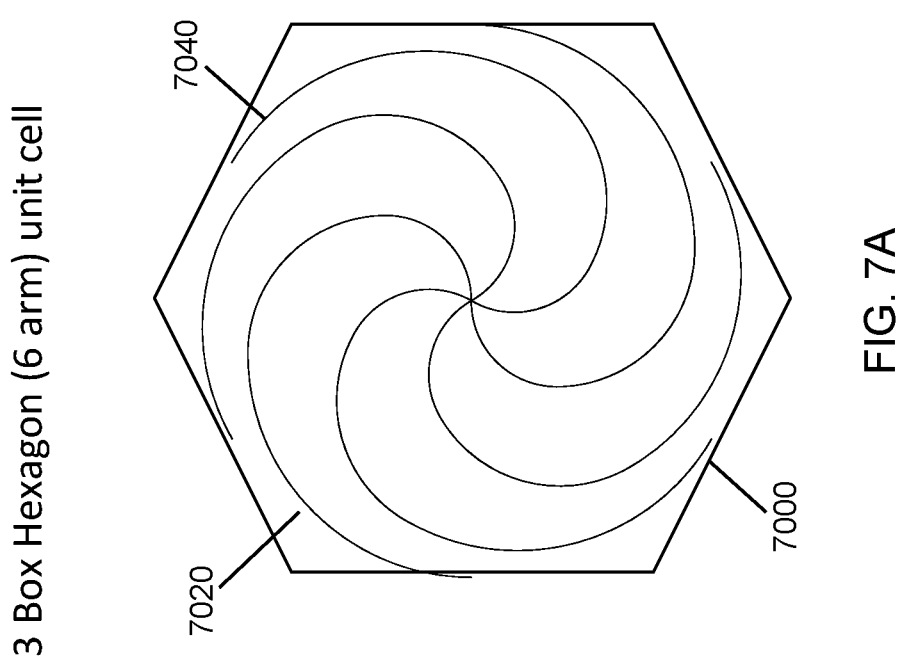
Figure 8B:
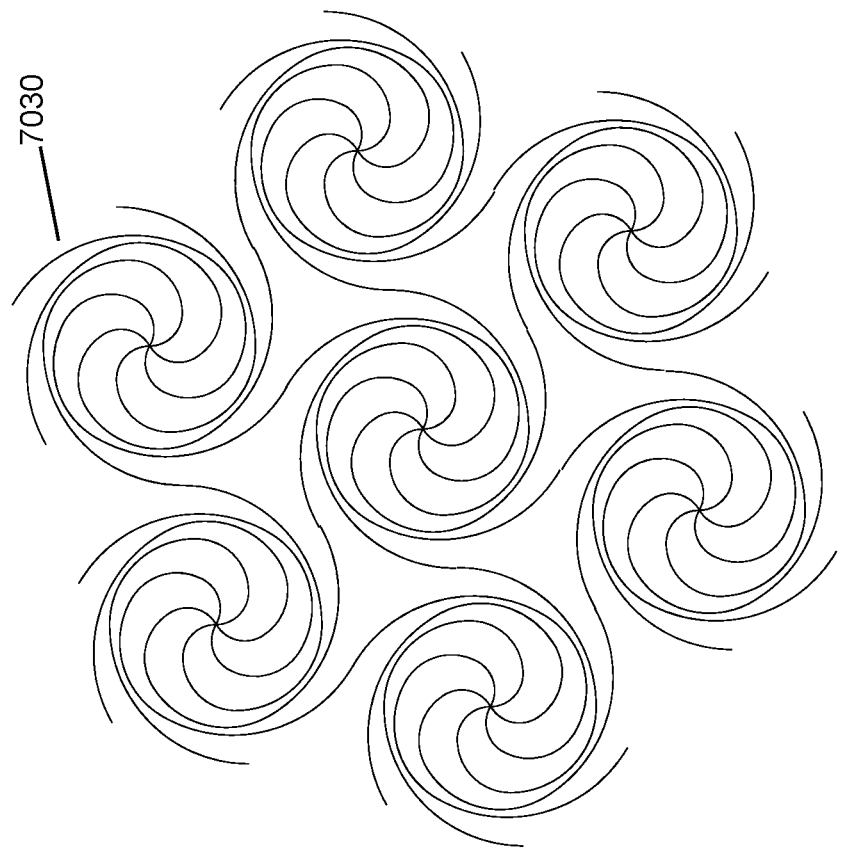
FIG. 8B illustrates an exemplary three box Phi spiral, hexagon-based system comprising a plurality of interconnected spirals of FIG. 7B according to an embodiment.
Figure 8A:
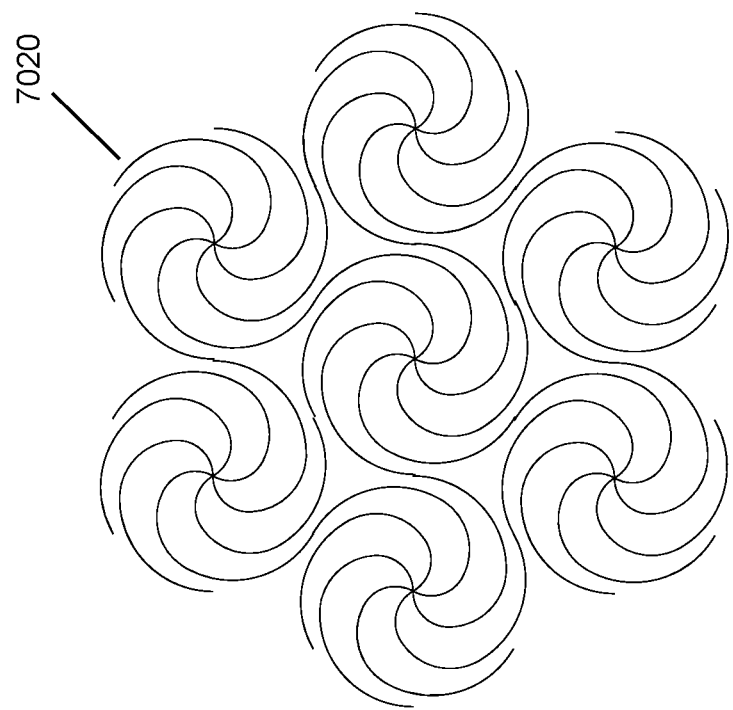
FIG. 8A illustrates an exemplary three box Phi spiral, hexagon-based system comprising a plurality of interconnected spirals of FIG. 7A according to an embodiment.

FIGS. 7A and 7B depict an exemplary three box Phi spiral, hexagon-shaped unit cell 7000 and an exemplary four box Phi spiral, hexagon-shaped unit cell 7010, respectively; where the hexagon-shaped unit cells 7000, 7010 of FIGS. 7A and 7B each comprise a spiral 7020, 7030 having six spiral arms 7040, 7050. FIG. 8A shows an exemplary three box Phi spiral, hexagon-based system comprising a plurality of interconnected spirals 7020 of three box Phi spiral, hexagon-shaped unit cells 7000; and FIG. 8B shows an exemplary four box Phi spiral, hexagon-based system comprising a plurality of interconnected spirals 7030 of four box Phi spiral, hexagon-shaped unit cells 7010. Although the systems depicted in FIGS. 8A and 8B each show a total of seven unit cells 7000, 7010, the thin-film mesh 110 may comprise more or less unit cells 7000, 7010 than is shown in FIGS. 8A and 8B.

Figure 9B:
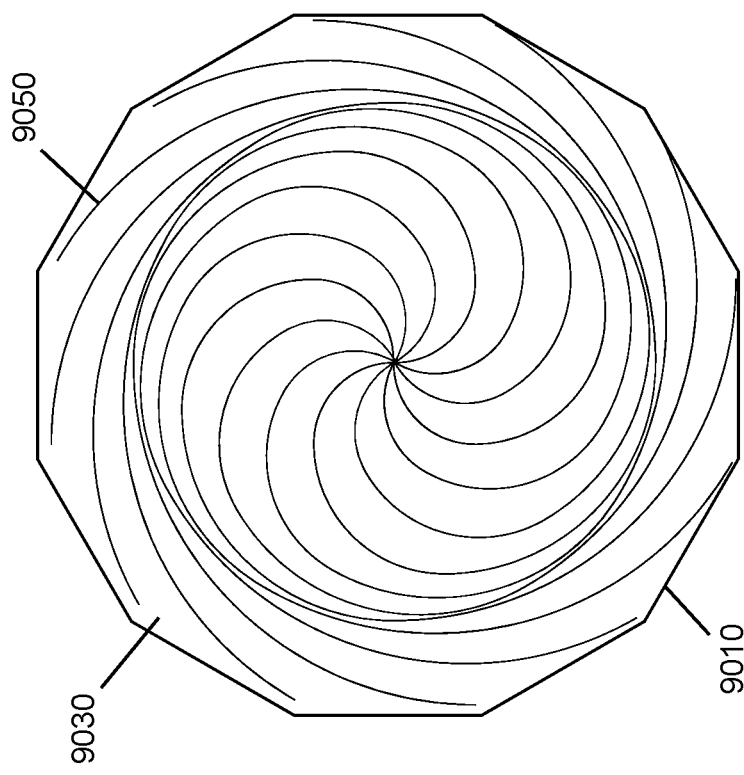
FIGS. 9A and 9B show two different types of box Phi spiral, dodecagon-shaped unit cells according to embodiments.
Figure 9A:
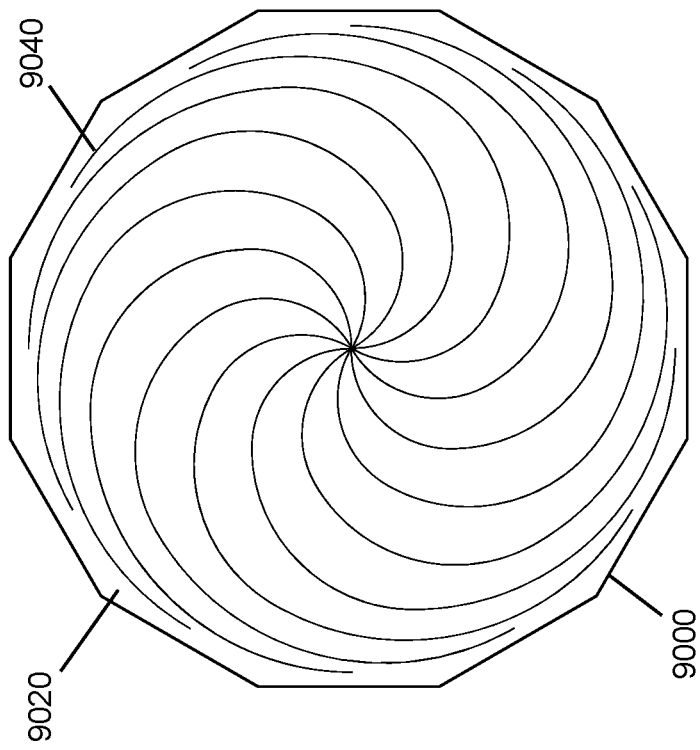
Figure 10A:
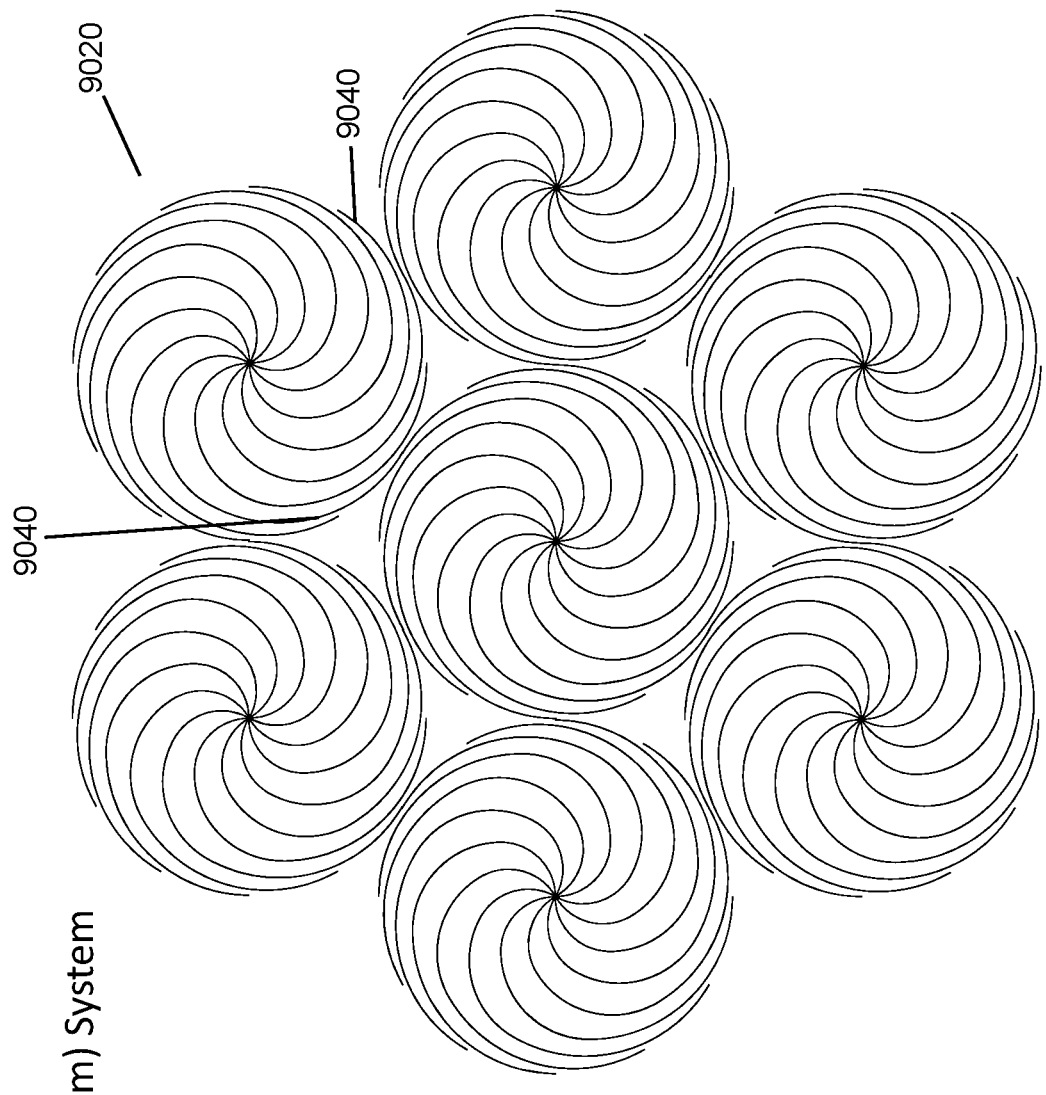
FIG. 10A illustrates an exemplary three box Phi spiral, dodecagon-based system comprising a plurality of interconnected spirals of FIG. 9A according to an embodiment.

FIGS. 9A and 9B depict an exemplary three box Phi spiral, dodecagon-shaped unit cell 9000 and an exemplary four box Phi spiral, dodecagon-shaped unit cell 9010, respectively; where the dodecagon-shaped unit cells 9000, 9010 of FIGS. 9A and 9B each comprise a spiral 9020, 9030 having twelve spiral arms 9040, 9050. FIG. 10A illustrates an exemplary three box Phi spiral, dodecagon-based system comprising a plurality of interconnected spirals 9020 of FIG. 9A. It should be noted that in the system of FIG. 10A, some of the spiral arms 9040 of the spirals 9020 of the three box Phi spiral, dodecagon-shaped unit cells 9000 are loose and are not connected to anything.

Figure 10B:
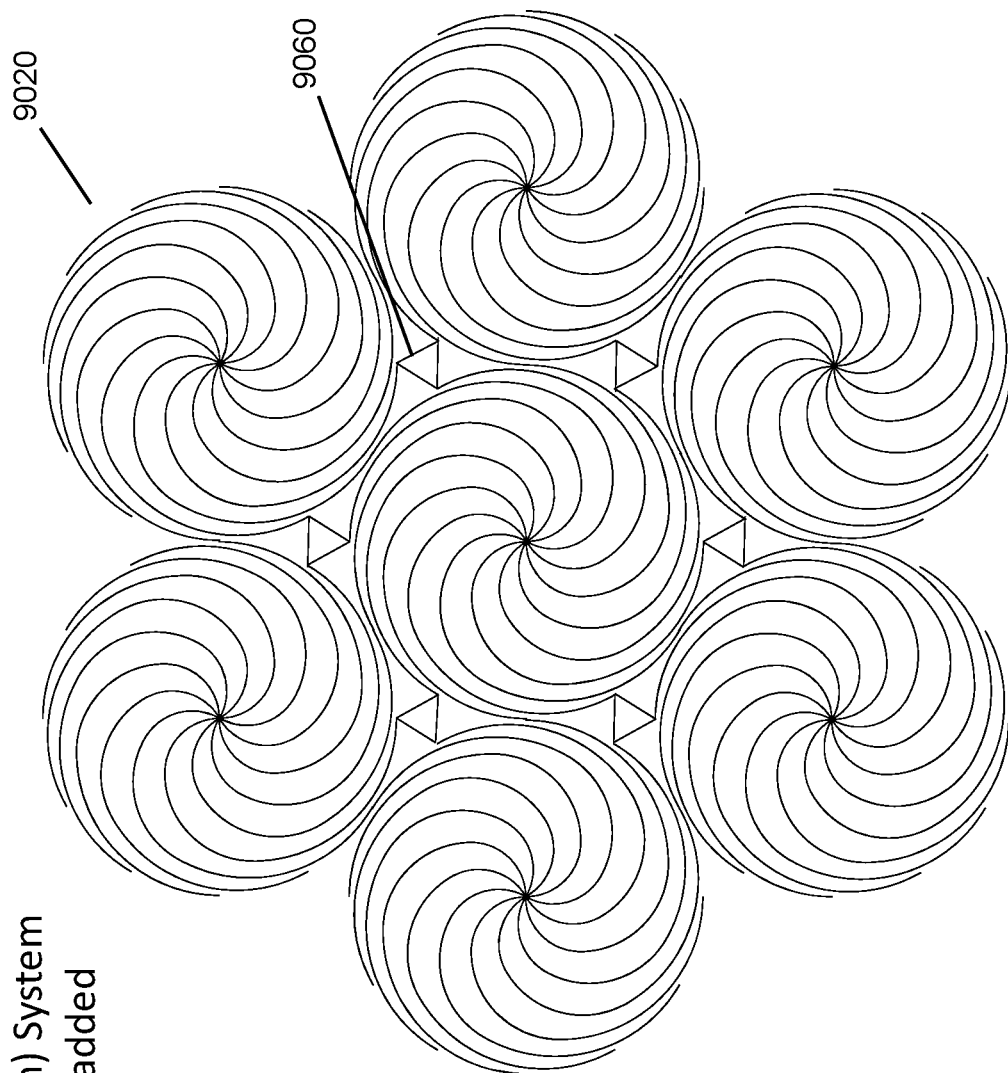
FIG. 10B illustrates an exemplary three box Phi spiral, dodecagon-based system comprising a plurality of interconnected spirals of FIG. 9A with triangular interconnects according to an embodiment.

In some embodiments, the spirals of the unit cells may be interconnected by an alternative means than by simply connecting the spiral arms together as is shown, for example, in FIG. 10A. For example, as shown in FIG. 10B, the plurality of interconnected spirals 9020 of FIG. 9A are connected together with triangular interconnects 9060. Each of the triangular interconnects 9060 connects three of the spirals 9020 together such that a spiral arm 9040 from each of the three spirals 9020 is connected respectively to a corner of the triangular interconnect 9060 as is shown in FIG. 10B. In other embodiments, interconnects of various different shapes other than a triangular shape as is shown in FIG. 10B may be employed by the thin-film mesh 110 to connect the spirals of the unit cells together.

Figure 10C:
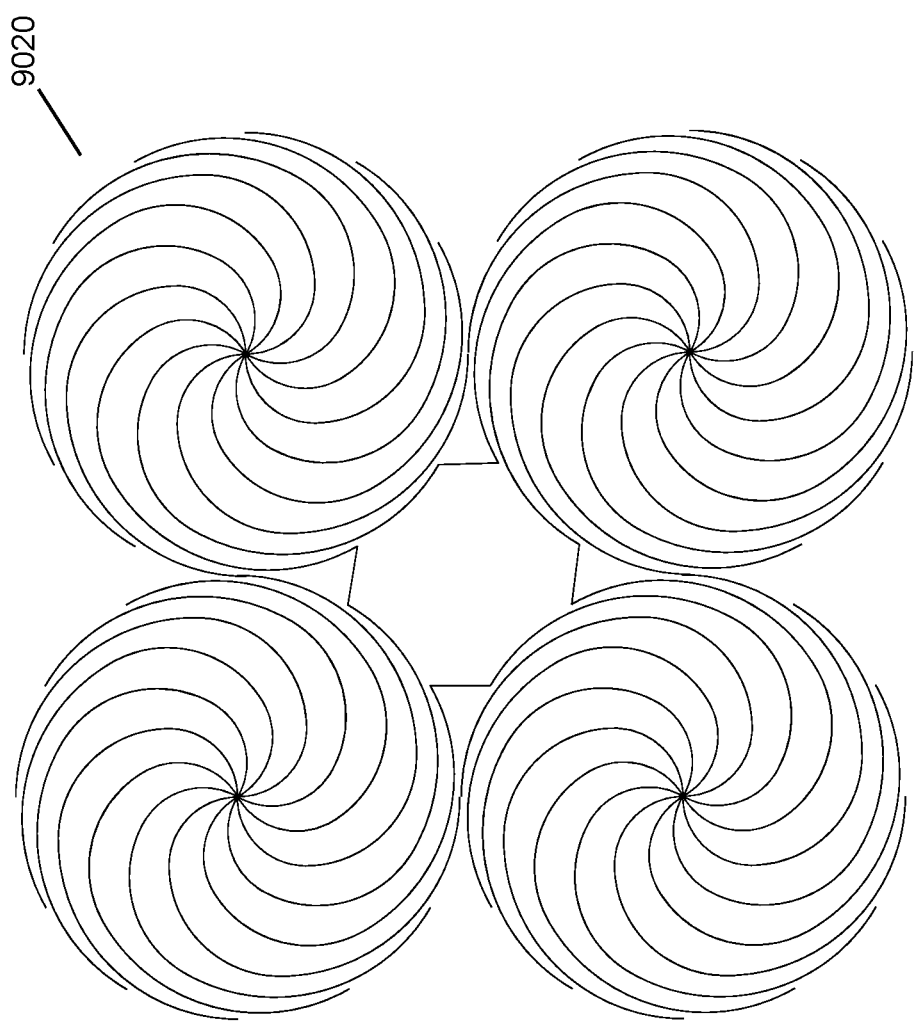
FIG. 10C illustrates another exemplary three box Phi spiral, dodecagon-based system comprising a plurality of interconnected spirals of FIG. 9A according to an embodiment.

In one or more embodiments, the unit cells of the thin-film mesh 110 may be tessellated in a variety of different alternative ways. For example, FIG. 10C illustrates another exemplary three box Phi spiral, dodecagon-based system comprising a plurality of interconnected spirals 9020 of FIG. 9A, where the unit cells 9000 of the system are tessellated differently than the unit cells 9000 as is shown in FIG. 10A.

Figure 11A:
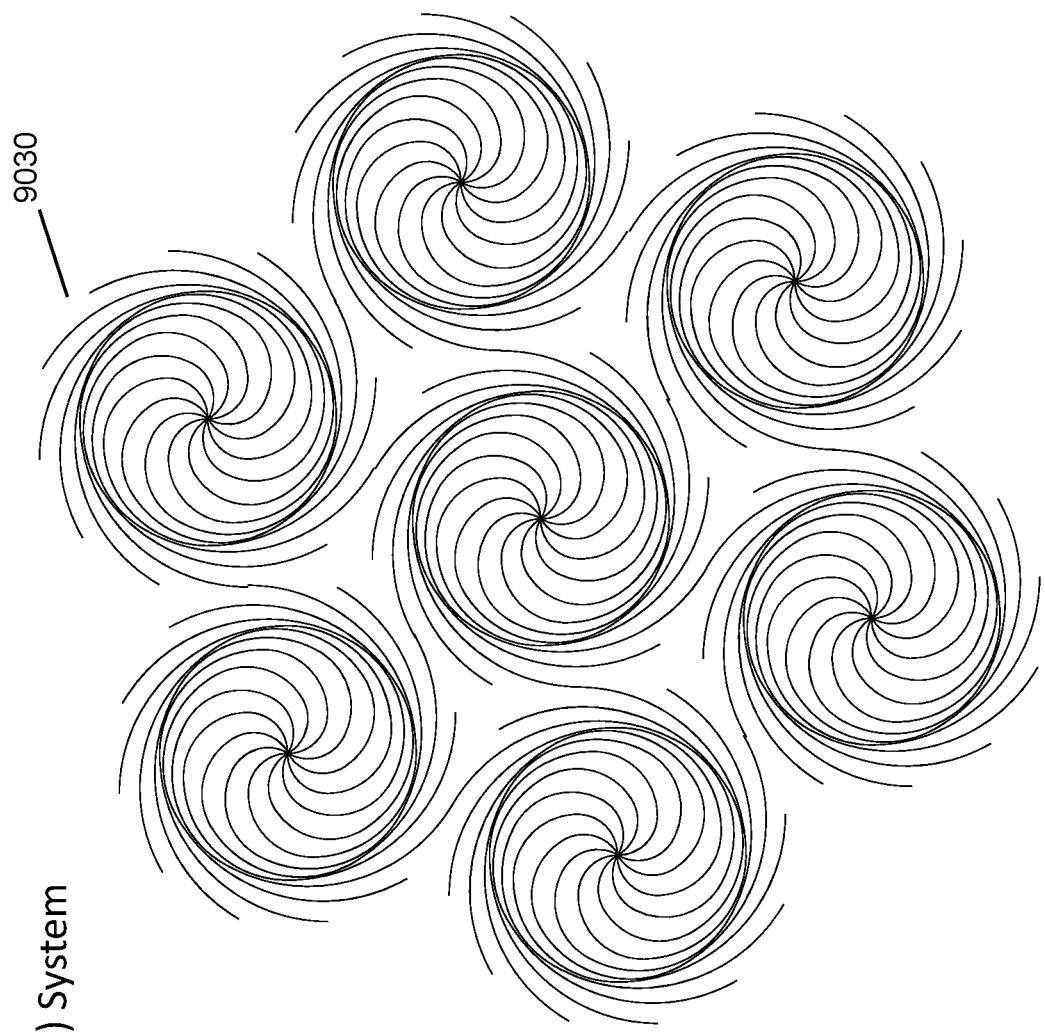
FIG. 11A illustrates an exemplary four box Phi spiral, dodecagon-based system comprising a plurality of interconnected spirals of FIG. 9B according to an embodiment.
Figure 11B:
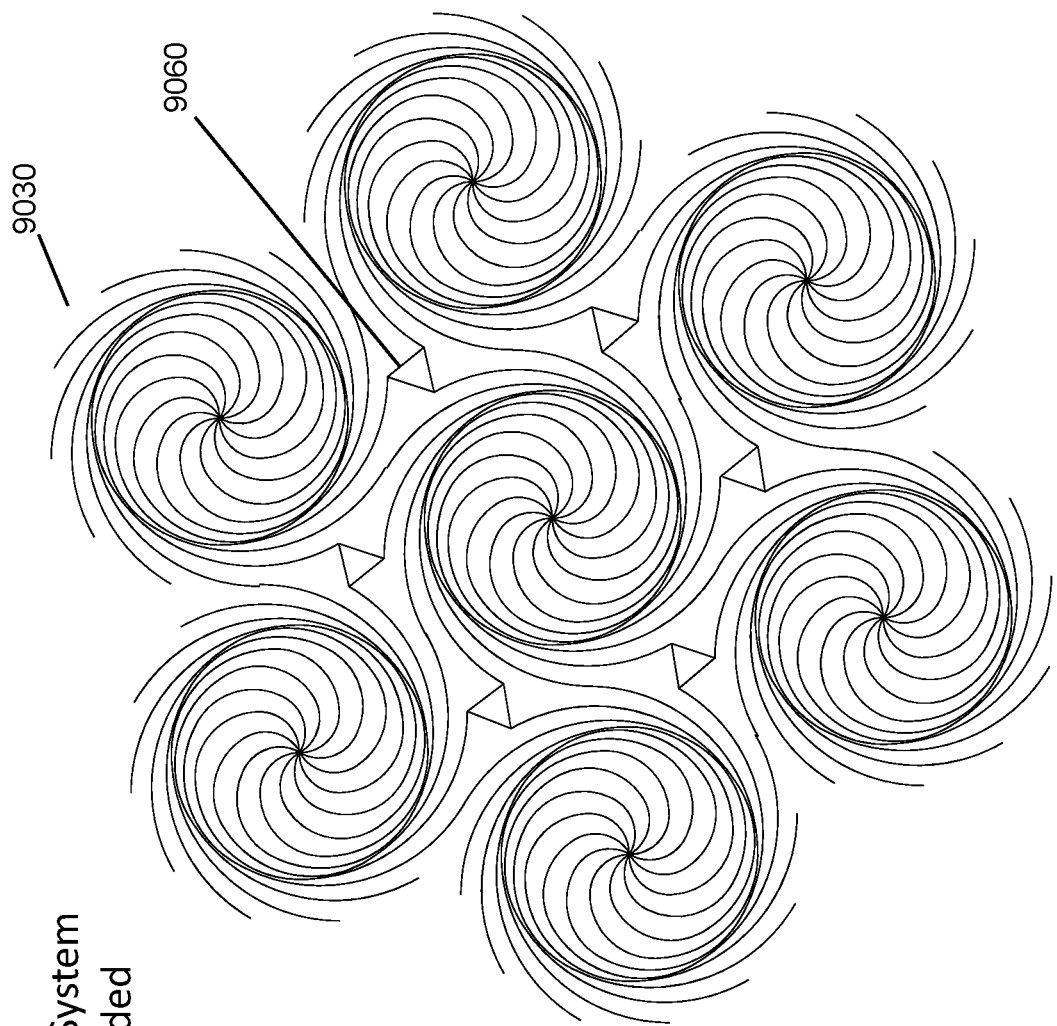
FIG. 11B illustrates an exemplary four box Phi spiral, dodecagon-based system comprising a plurality of interconnected spirals of FIG. 9B with triangular interconnects according to an embodiment.
Figure 12:
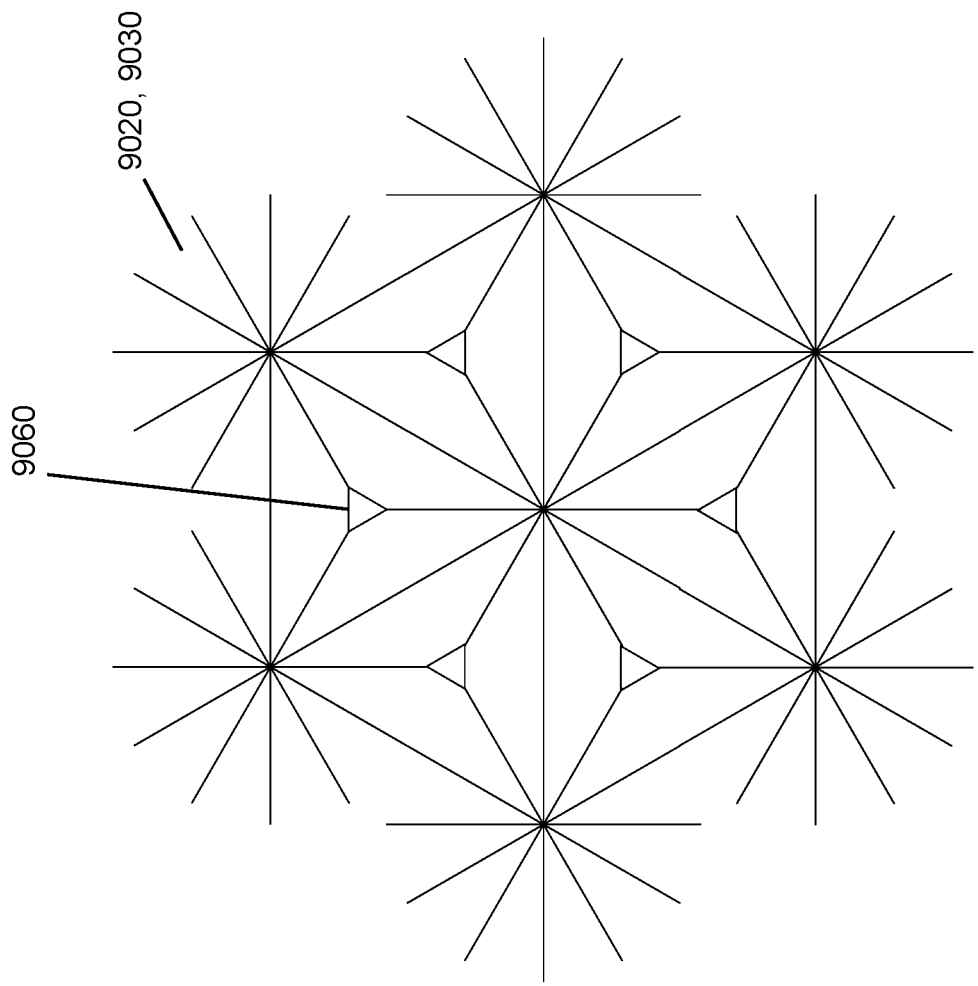
FIG. 12 illustrates a spiral dodecagon-based system comprising a plurality of interconnected spirals of FIG. 9A or 9B with triangular interconnects stretched out at theoretical full expansion according to an embodiment.

FIG. 11A illustrates an exemplary four box Phi spiral, dodecagon-based system comprising a plurality of interconnected spirals 9030 of FIG. 9B. And, in FIG. 11B, the plurality of interconnected spirals 9030 of FIG. 9B are connected together with triangular interconnects 9060. For theoretical purposes to show the full expansion of an exemplary thin-film mesh 110, FIG. 12 shows a spiral dodecagon-based system comprising a plurality of interconnected spirals 9020, 9030 of FIG. 9A or 9B with triangular interconnects 9060 stretched out at theoretical full expansion.

Figure 14A:
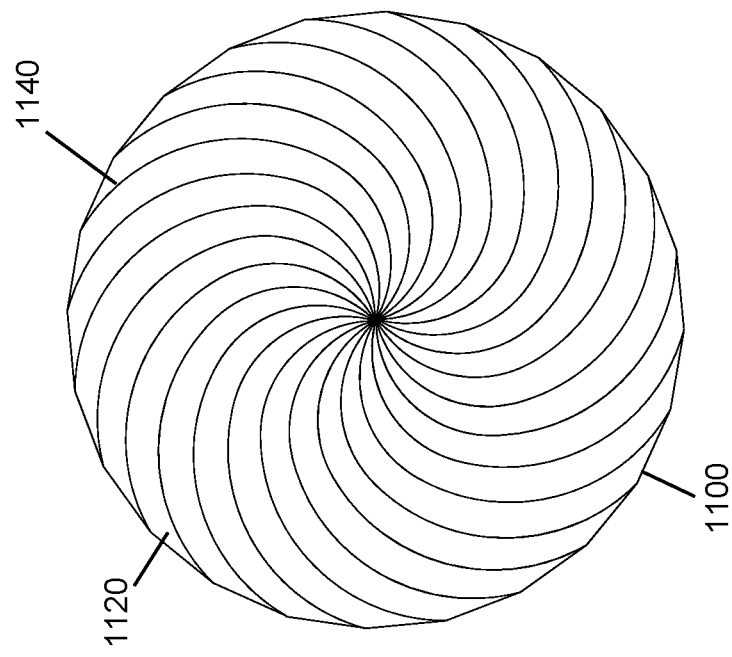
FIG. 14A illustrates a two box Phi spiral, icositetragon-shaped unit cell comprising twenty-four arms according to an embodiment.
Figure 14B:
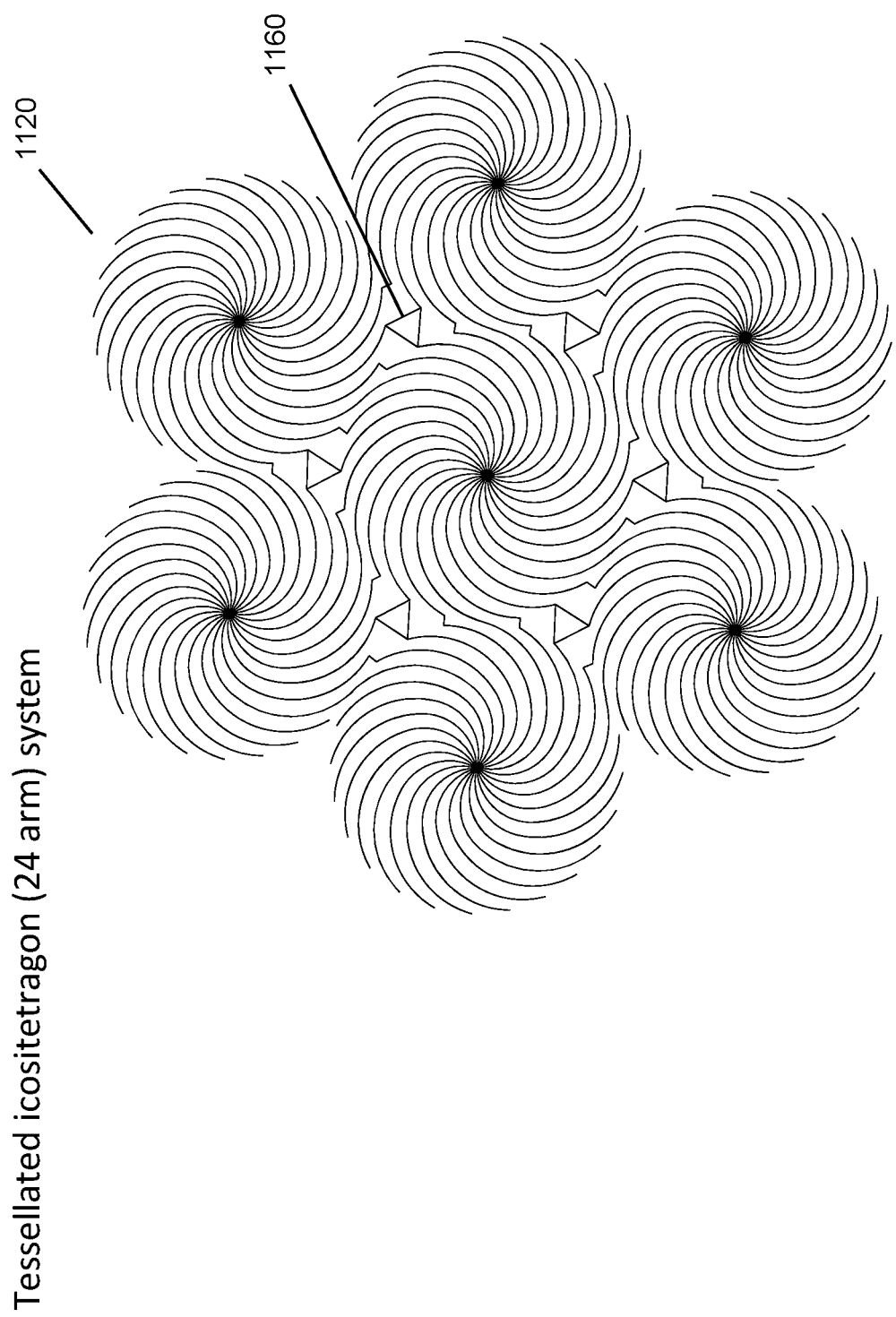
FIG. 14B illustrates an exemplary two box Phi spiral, icositetragon-based system comprising a plurality of interconnected spirals of FIG. 14A with triangular interconnects according to an embodiment.

FIG. 14A depicts an exemplary two box Phi spiral, icositetragon-shaped unit cell 1100, where the icositetragon-shaped unit cell 1100 of FIG. 14A comprises a spiral 1120 having twenty-four spiral arms 1140. FIG. 14B illustrates an exemplary two box Phi spiral, icositetragon-based system comprising a plurality of interconnected spirals 1120 of FIG. 14A with triangular interconnects 1160 according to an embodiment. Each of the triangular interconnects 1160 connects three of the spirals 1120 together such that a spiral arm 1140 from each of the three spirals 1120 is connected respectively to a corner of the triangular interconnect 1160 as is shown in FIG. 14B.

Figure 15A:
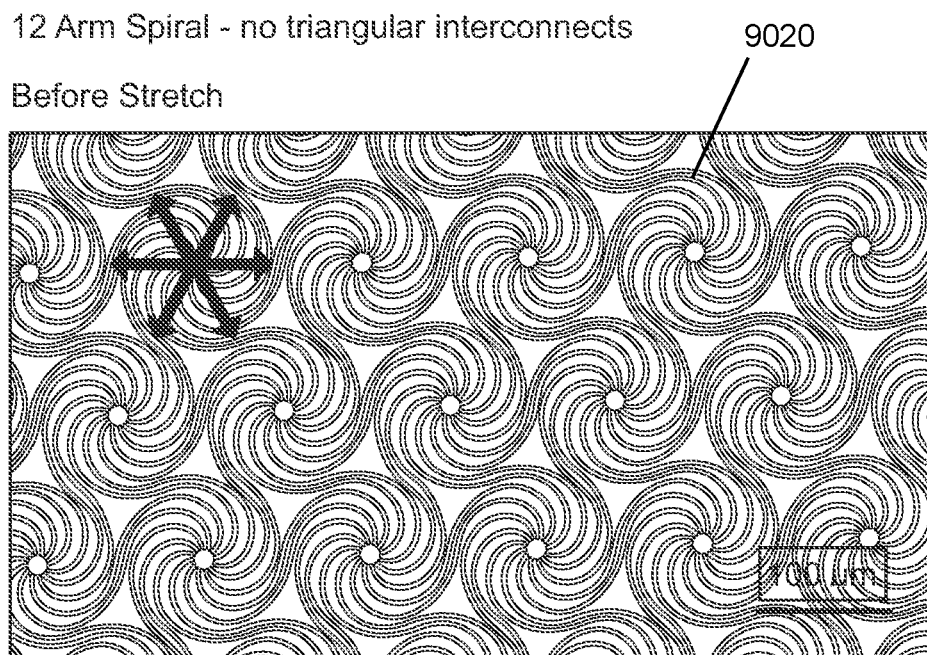
FIG. 15A illustrates a portion of a thin-film mesh comprising a three box Phi spiral, dodecagon-based system comprising a plurality of interconnected spirals of FIG. 9A that are unstretched according to an embodiment.

FIGS. 15A-17B show portions of thin-film meshes 110 in unstretched states and stretched states. For example, FIG. 15A illustrates a portion of a thin-film mesh 110 comprising a three box Phi spiral, dodecagon-based system comprising a plurality of interconnected spirals 9020 of FIG. 9A that are unstretched (i.e. in an unstretched state). FIG. 15B illustrates a portion of a thin-film mesh 110 comprising a three box Phi spiral, dodecagon-based system comprising a plurality of interconnected spirals 9020 of FIG. 9A that are stretched (i.e. in a stretched state).

Figure 15B:
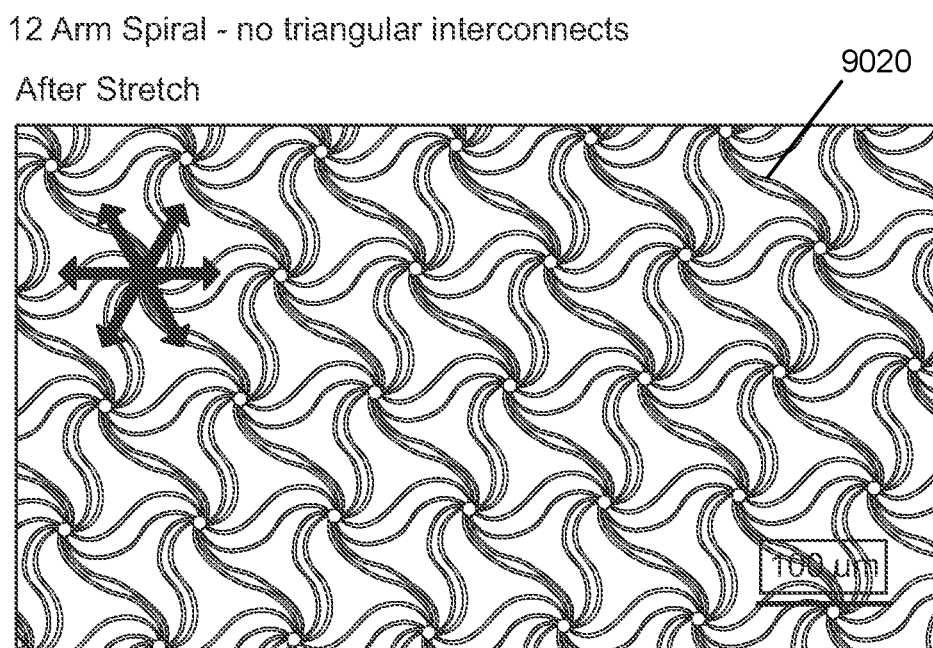
FIG. 15B illustrates a portion of a thin-film mesh comprising a three box Phi spiral, dodecagon-based system comprising a plurality of interconnected spirals of FIG. 9A that are stretched according to an embodiment.

The spirals 9020 in FIGS. 15A and 15B are interconnected by connecting the spiral arms 9040 of the different spirals 9020 together. This types of interconnection allows for the spirals 9020 to have three axes of stretch. Each of the spiral arms 9040 of the spirals 9020 may be approximately 3 microns in width. Experimental data shows that with the spiral arms 9040 being approximately 3 microns in width, when the spirals 9020 are unstretched (i.e. in an unstretched state), the node (e.g., center of the spiral) to node (e.g., center of the spiral) distance is approximately 130 µm. And, when the spirals 9020 are stretched (i.e. in a stretched state), the node (e.g., center of the spiral) to node (e.g., center of the spiral) distance is approximately 220 µm. As such, the percentage of stretch per axis is approximately 67 percent. This provides an increase in surface area of the thin-film mesh 110 of approximately 270 percent.

Figure 16A:
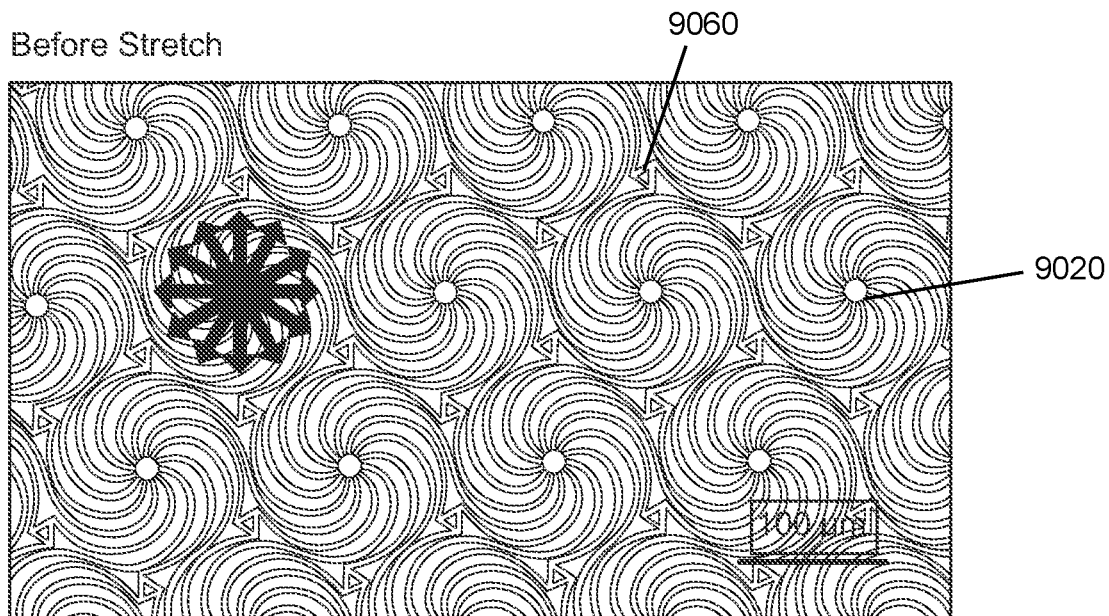
FIG. 16A illustrates a portion of a thin-film mesh comprising a three box Phi spiral, dodecagon-based system comprising a plurality of interconnected spirals of FIG. 9A with triangular interconnects that are unstretched according to an embodiment.

FIGS. 16A-17B show portions of thin-film meshes 110 that comprise triangular interconnects 9060 in unstretched states and stretched states. In particular, FIG. 16A illustrates a portion of a thin-film mesh 110 comprising a three box Phi spiral, dodecagon-based system comprising a plurality of interconnected spirals 9020 of FIG. 9A with triangular interconnects 9060 that are unstretched (i.e. in an unstretched state). FIG. 16B illustrates a portion of a thin-film mesh 110 comprising a three box Phi spiral, dodecagon-based system comprising a plurality of interconnected spirals 9020 of FIG. 9A with triangular interconnects 9060 that are stretched (i.e. in a stretched state).

Figure 16B:
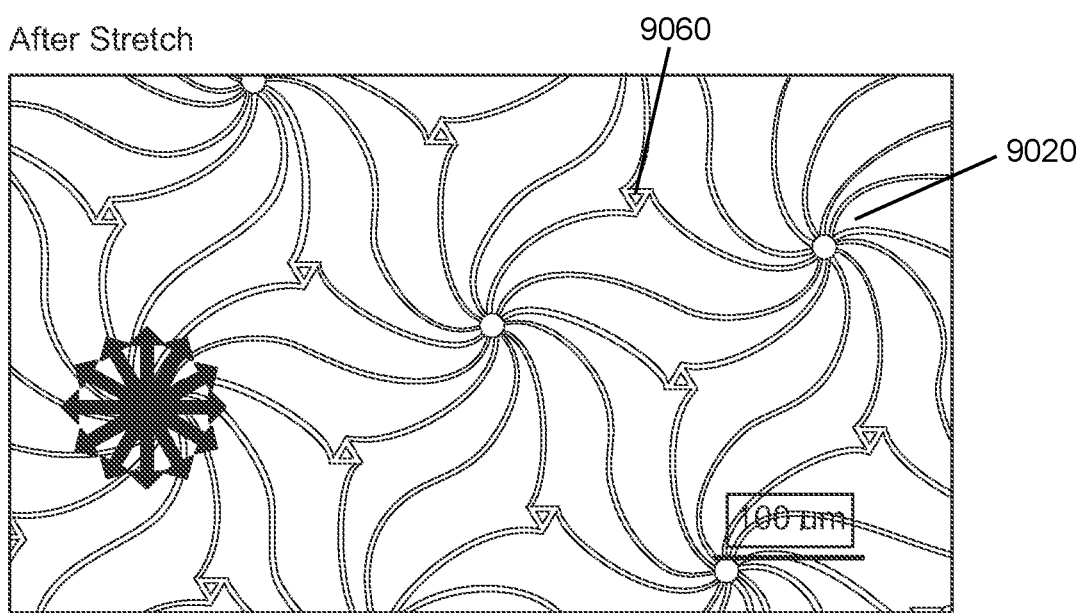
FIG. 16B illustrates a portion of a thin-film mesh comprising a three box Phi spiral, dodecagon-based system comprising a plurality of interconnected spirals of FIG. 9A with triangular interconnects that are stretched according to an embodiment.

The spirals 9020 in FIGS. 16A and 16B are interconnected by connecting the spiral arms 9040 of the different spirals 9020 together via triangular interconnects 9060. This type of interconnection allows for the spirals 9020 to have six axes of stretch. Each of the spiral arms 9040 of the spirals 9020 may be approximately 3 microns in width. Experimental data shows that with the spiral arms 9040 being approximately 3 microns in width, when the spirals 9020 are unstretched (i.e. in an unstretched state), the node (e.g., center of the spiral) to node (e.g., center of the spiral) distance is approximately 130 µm. And, when the spirals 9020 are stretched (i.e. in a stretched state), the node (e.g., center of the spiral) to node (e.g., center of the spiral) distance is approximately 270 µm. The percentage of stretch per axis is approximately 68 percent. This gives an increase in surface area of the thin-film mesh 110 of approximately 280 percent. This design also provides a pore density of approximately 150 pores per mm$^2$, and the largest strut-to-strut distance is approximately 50 µm.

Figure 17A:
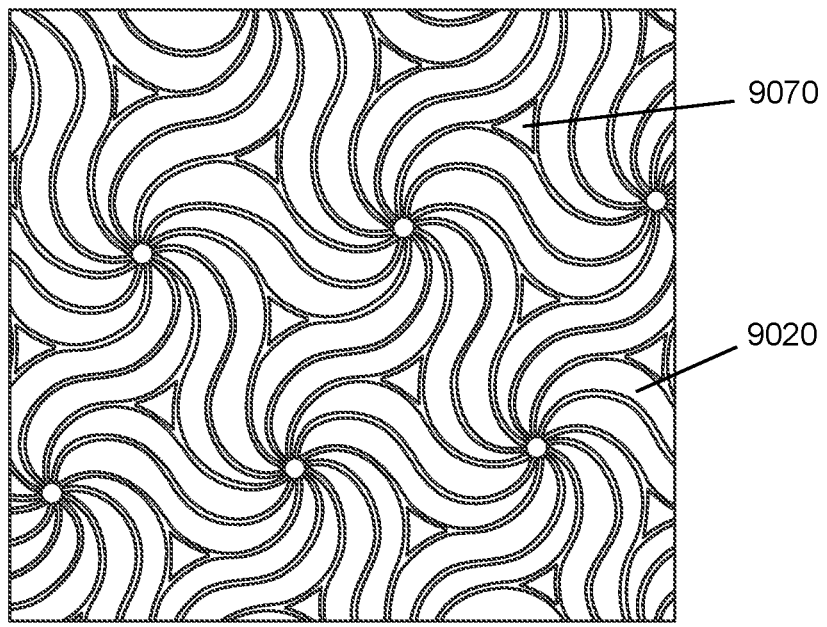
FIG. 17A illustrates a portion of a thin-film mesh comprising a three box Phi spiral, dodecagon-based system comprising a plurality of interconnected spirals of FIG. 9A with alternative triangular interconnects that are stretched according to an embodiment.
Figure 17B:
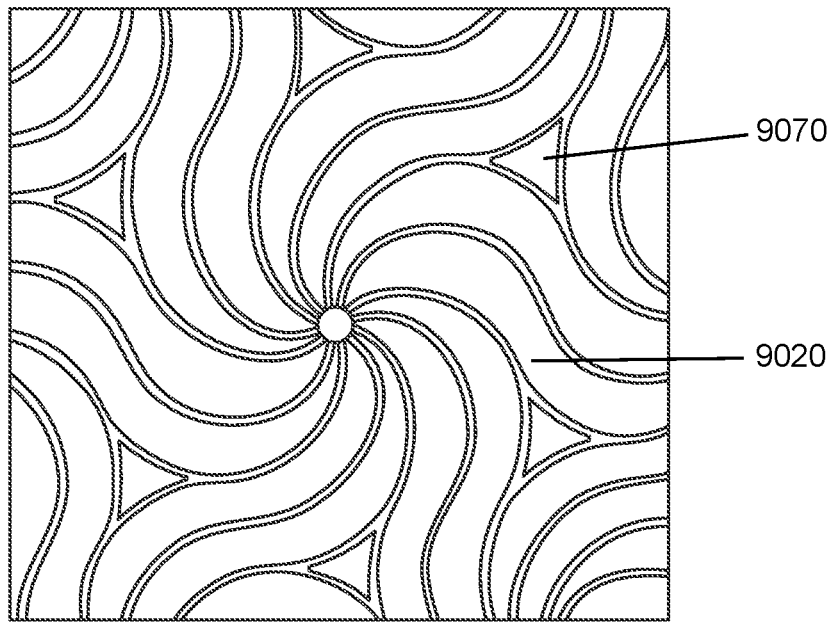
FIG. 17B illustrates a close-up view of a portion of the thin-film mesh of FIG. 17A according to an embodiment.

FIGS. 17A and 17B show portions of thin-film meshes 110 that comprise alternative triangular interconnects 9070 in unstretched states and stretched states. The triangular interconnects 9070 in FIGS. 17A and 17B are designed differently than the triangular interconnects 9060 of FIGS. 16A and 16B such that the triangular interconnects 9070 of FIGS. 17A and 17B are rotated at an angle to allow for more efficient packing of the unit cells 9000 of the thin-film mesh 110. FIG. 17A illustrates a portion of a thin-film mesh 110 comprising a three box Phi spiral, dodecagon-based system comprising a plurality of interconnected spirals 9020 of FIG. 9A with the alternative triangular interconnects 9070. FIG. 17B illustrates a close-up view of a portion of the thin-film mesh 110 of FIG. 17A.

IV. Spiral-Based Thin-Film Mesh Device with Anti-Prolapse Backbone Design

Figure 18:
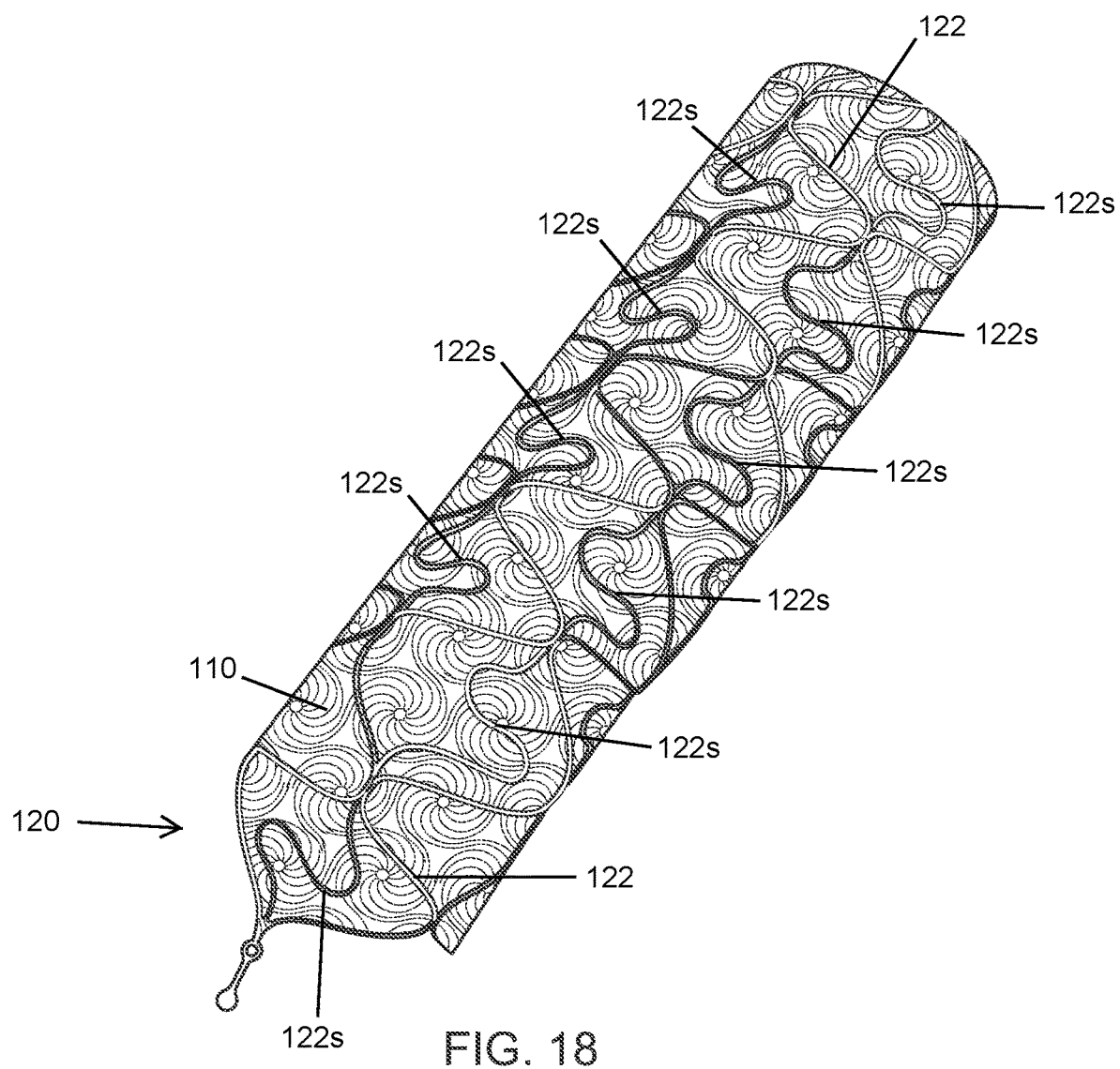
FIG. 18 is a diagrammatic perspective view of a thin-film mesh device (e.g., an endovascular stent) covered with a thin-film mesh cover (e.g., a stent cover) according to an embodiment.

The thin-film mesh 110 may be employed in a thin-film mesh device 120, such as an endovascular stent. FIG. 18 shows a thin-film mesh device (e.g., an endovascular stent) 120 covered with a thin-film mesh 110. The thin-film mesh device 120 may include a backbone (e.g., a stent backbone) 122 comprising an undulating curve shape that further comprises a plurality of S-shapes 122s mounted in between the undulations of the curve shape, as is shown in FIG. 18. The S-shapes 122s incorporated into the backbone 122 prevent the thin-film mesh 110 of the thin-film device 120 from experiencing prolapse when the thin-film device 120 is contoured or bent.

Figure 19A:
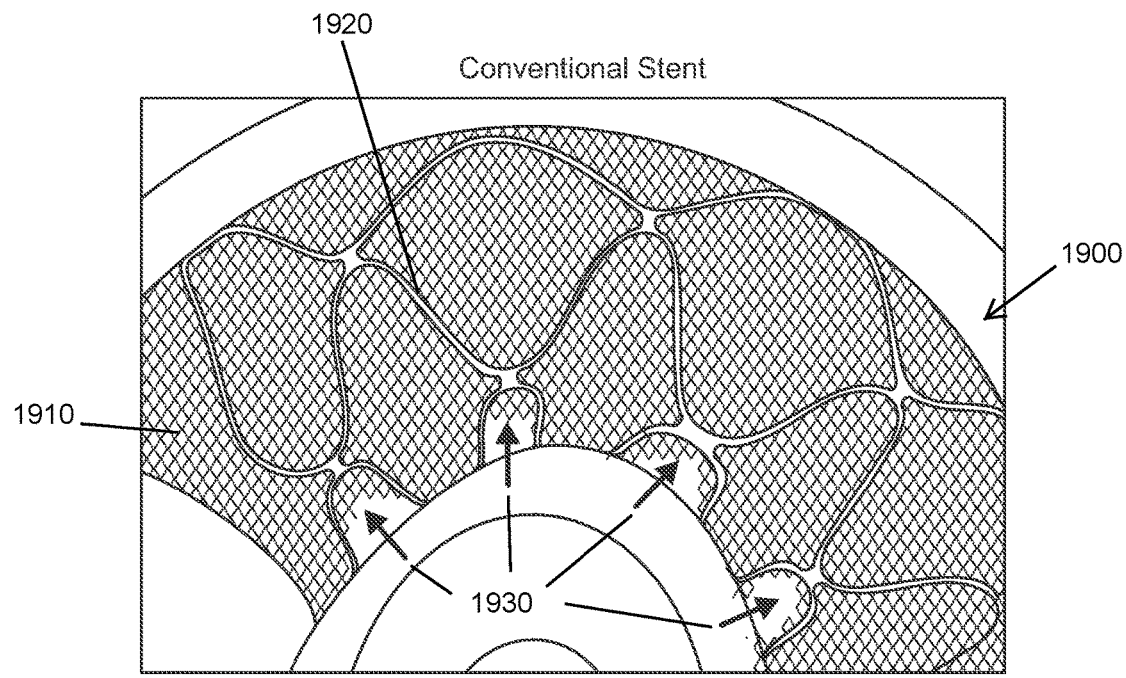
FIG. 19A is an image of a conventional thin-film mesh device contoured or bent exhibiting prolapse.
Figure 19B:
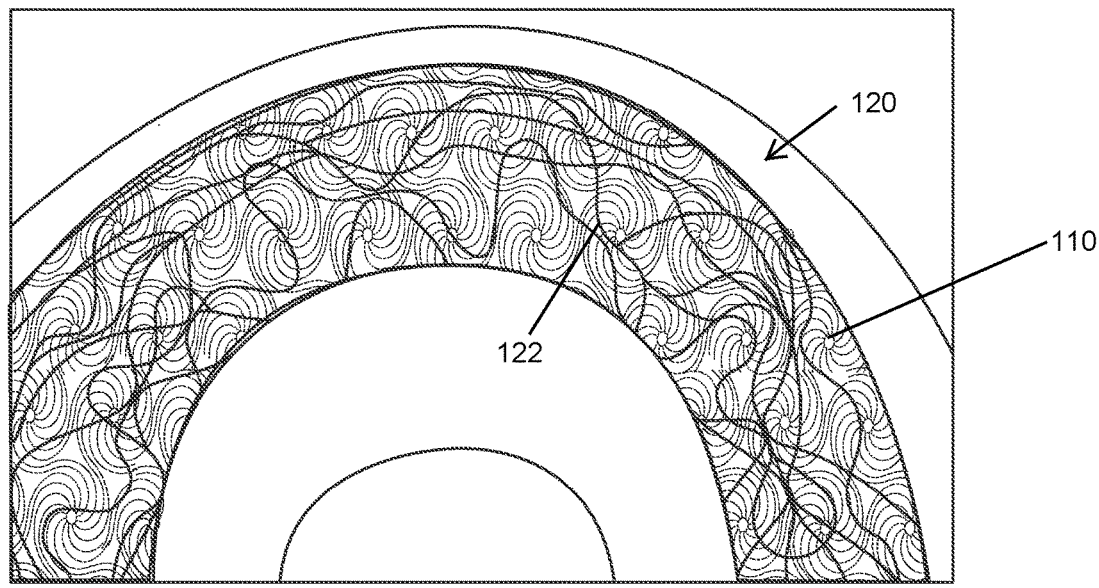
FIG. 19B is an image of a thin-film mesh device contoured or bent not exhibiting prolapse according to an embodiment.

For example, FIG. 19A shows a stent cover 1910 of a conventional endovascular stent 1900 exhibiting prolapse 1930 when the stent 1900 is contoured or bent. The stent 1900 comprises a conventional backbone 1920 that includes an undulating curve shape with no additional structure included in the backbone 1920 (e.g., no additional structure is included within the undulating curve shape of the backbone 1920). When the conventional stent 1900 is bent, the stent cover 1910 experiences prolapse 1930, which affects the integrity and functionality of the stent 1900. FIG. 19B shows the thin-film mesh device 120 of FIG. 19A being contoured or bent without exhibiting prolapse because of the addition of the S-shaped curves 122s within the backbone 122 of the thin-film mesh device 120.

V. Manufacturing Process for Spiral-Based Thin-Film Mesh

Figure 20:
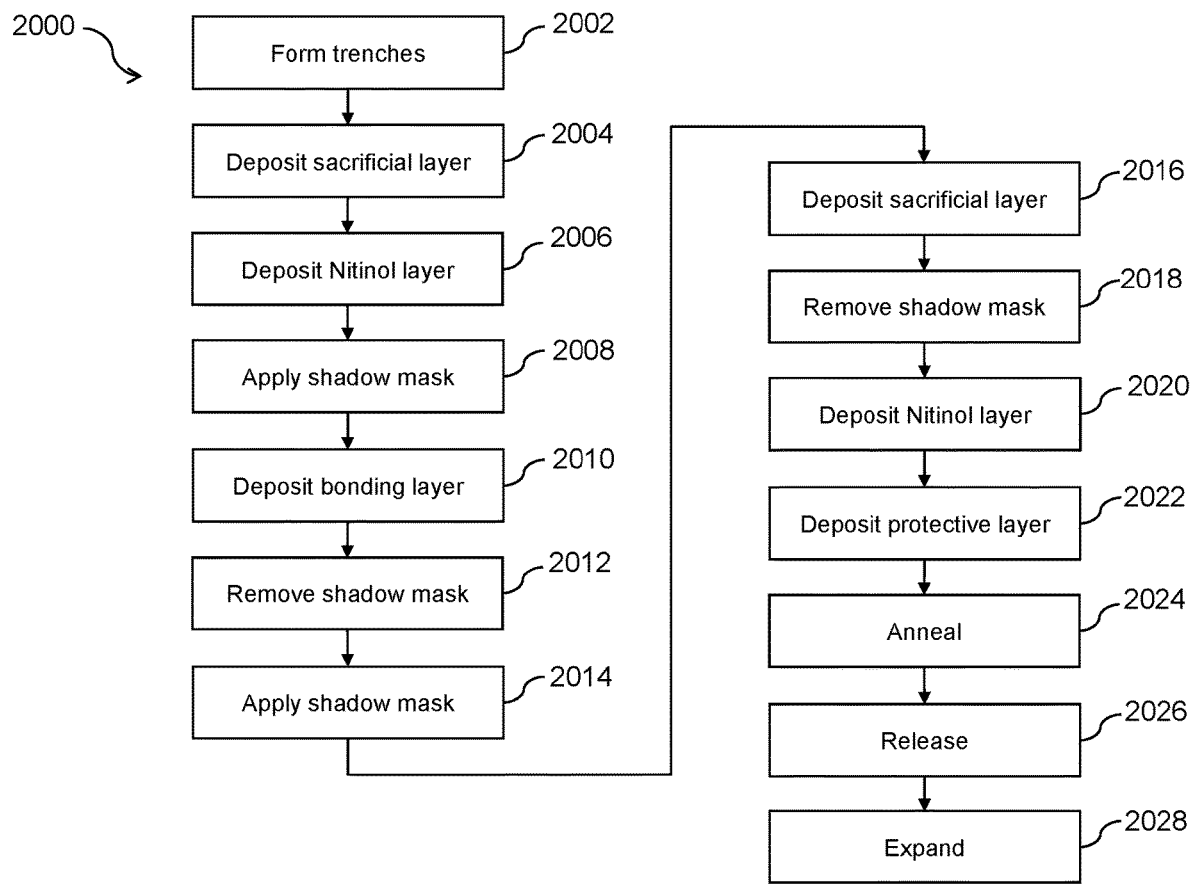
FIG. 20 is a flow diagram of a process to fabricate a thin-film mesh for a medical device according to an embodiment.
Figure 21A:
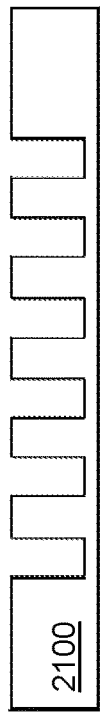
FIGS. 21A-21Q are diagrammatic cross-sectional views of layers being formed on a substrate to fabricate a thin-film mesh according to an embodiment.
Figure 21B:
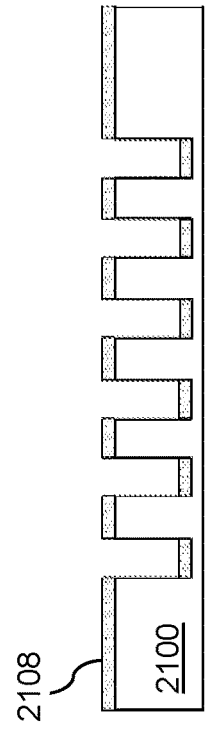
Figure 21C:
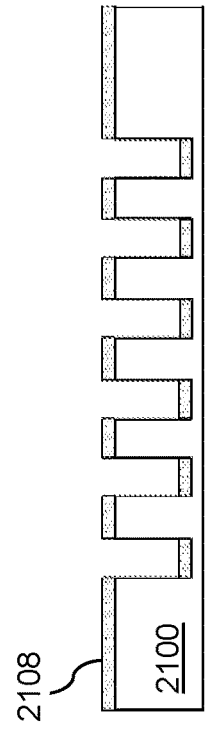
Figure 21D:
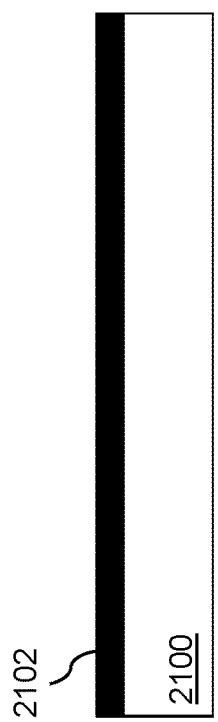
Figure 21E:
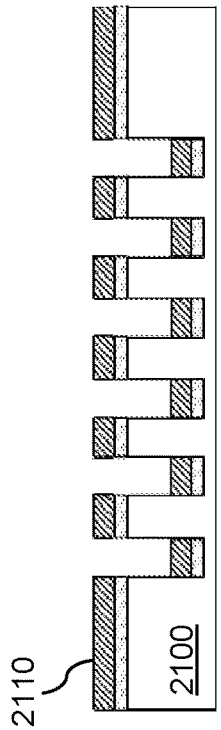

FIG. 20 is a flow diagram of a process 2000 to fabricate a thin-film mesh, such as thin-film mesh 110, for a thin-film mesh device, such as thin-film mesh device 120. At block 2002, trenches are formed on a wafer 2100 (e.g., a silicon wafer or other wafer) as shown in FIGS. 21A-21E. FIG. 21A shows wafer 2100, which may have an oxide layer with a thickness of between 500 nanometers (nm) and 1 micrometers (µm) on top. A photoresist 2102 is spun-coated on wafer 2100 as shown in FIG. 21B. By patterning and developing photoresist 2102 using photolithography, a pattern of exposed areas 2104 is formed as shown in FIG. 21C. The pattern may define negative areas of spirals and/or negative areas of interconnects, such as triangular interconnects. The pattern of exposed areas 2104 is available for etching. Deep reactive ion etching (DRIE) is performed to form grooves or trenches 2106 that are at least 15 µm deep (e.g., between 25 µm and 200 µm deep) as shown in FIG. 21D. Photoresist 2102 is removed and wafer 2100 is cleaned, resulting in etched wafer 2100 with trenches 2106 as shown in FIG. 21E. Trenches 2106 may form a micropattern that provides a template for thin-film mesh 210. For example, the micropattern may define negative areas of spirals, such as shown in FIGS. 15A-17B. The resolution of the micropattern using the DRIE process may be, for example, approximately 1 µm. Wafer 2100 may include a plurality of micropatterns. The term "approximately," as used herein when referring to a measurable value, encompasses variations of ±20%, ±10%, ±5%, ±1%, ±0.5%, or ±0.1% of the value.

Figure 21F:
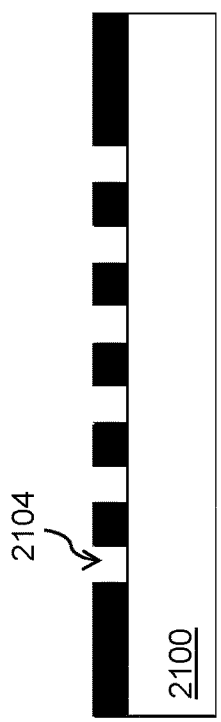

At block 2004, a sacrificial layer 2108 (e.g., a chrome sacrificial layer or a copper sacrificial layer), also referred to as a lift-off layer, is deposited as shown in FIG. 21F. Sacrificial layer 2108 may be deposited by sputter deposition or evaporation deposition such as electron beam physical vapor deposition (EBPVD). Sacrificial layer 2108 may have a thickness of, for example, 1 µm or less (e.g., approximately 500 nm).

Figure 21G:
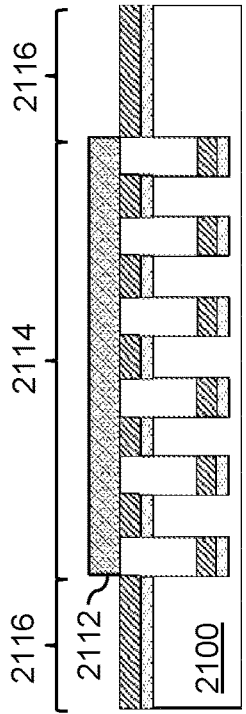

At block 2006, a Nitinol layer 2110 is deposited as shown in FIG. 21G. Nitinol layer 2110 may have a thickness of, for example, between 1 µm and 20 µm (e.g., approximately 5 µm). As sputtered Nitinol at regions corresponding to trenches 2106 fall to the bottom of trenches 2106, the micropattern of trenches 2106 of wafer 2100 are duplicated on Nitinol layer 2110 as corresponding fenestrations (e.g., closed fenestrations) such as negative areas of spirals of thin-film mesh 110, such as shown in FIGS. 15A-17B. The resulting pattern of fenestrations may also be denoted as a fiche in that fenestrations are in closed form (e.g., refer to FIGS. 15A and 16A) prior to an expansion of thin-film mesh 110. Just like a microfiche, each fiche or pattern of fenestrations effectively codes for resulting fenestrations when thin-film mesh 110 is expanded (e.g., refer to FIGS. 15B and 16B) to fully open up fenestrations.

Figure 21H:
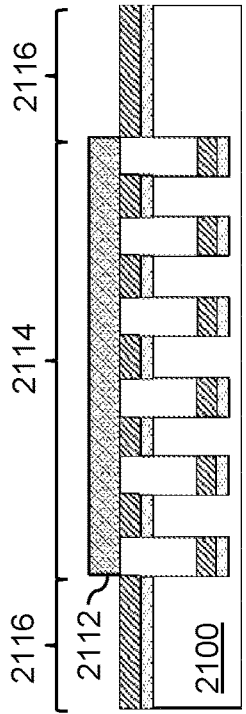

At block 2008, a shadow mask 2112 is applied as shown in FIG. 21H. Shadow mask 2112 is applied to a mesh region 2114 and exposes seam regions 2116 for deposition of a bonding layer 2118.

Figure 21L:
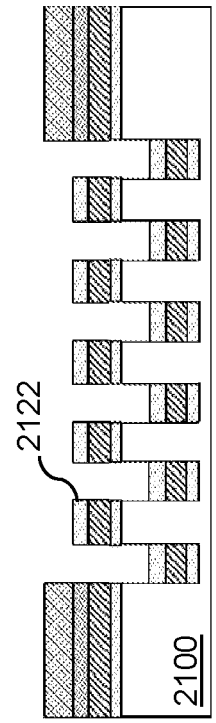
Figure 21M:
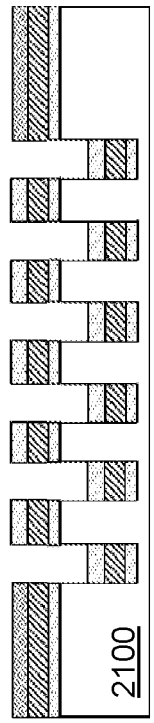
Figure 21N:
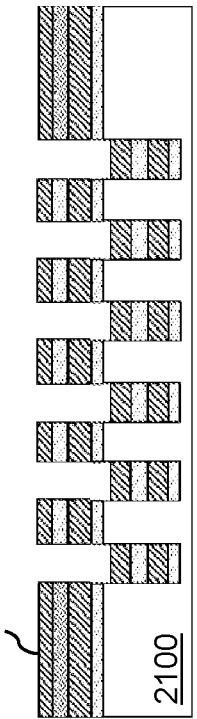
Figure 21I:
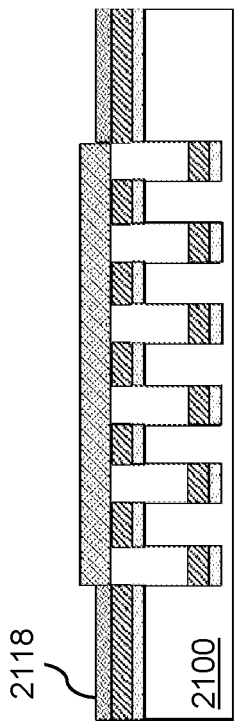

At block 2010, bonding layer 2118 (e.g., an aluminum bonding layer) is deposited as shown in FIG. 21I. Bonding layer 2118 may have a thickness of, for example, 1 µm or less (e.g., approximately 500 nm).

Figure 21J:
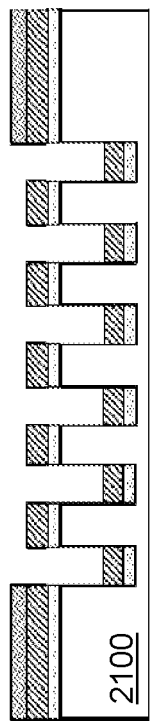

At block 2012, shadow mask 2112 is removed as shown in FIG. 21J.

Figure 21K:
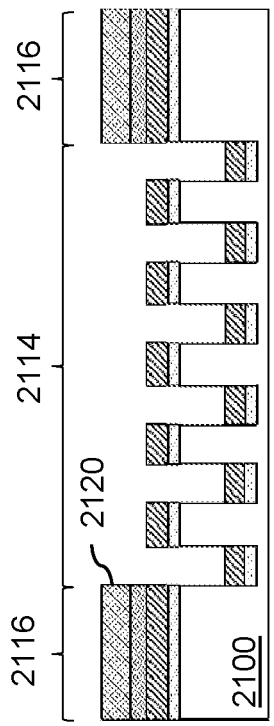

At block 2014, a shadow mask 2120 is applied as shown in FIG. 21K. Shadow mask 2120 is applied to seam regions 2116 and exposes mesh region 2114 for deposition of a sacrificial layer 2122.

At block 2016, sacrificial layer 2122 (e.g., a chrome sacrificial layer or a copper sacrificial layer) is deposited as shown in FIG. 21L. Sacrificial layer 2122 may have a thickness of, for example, 1 µm or less (e.g., approximately 500 nm).

At block 2018, shadow mask 2120 is removed as shown in FIG. 21M.

At block 2020, a Nitinol layer 2124 is deposited as shown in FIG. 21N. Nitinol layer 2124 may have a thickness of, for example, between 1 µm and 50 µm (e.g., approximately 5 µm). Similarly to block 2006, as sputtered Nitinol at regions corresponding to trenches 2106 fall to the bottom of trenches 2106, the micropattern of trenches 2106 of wafer 2100 are duplicated on Nitinol layer 2124 as corresponding fenestrations (e.g., closed fenestrations) such as negative areas of spirals of thin-film mesh 110, such as shown in FIGS. 15A and 16A.

Figure 21O:
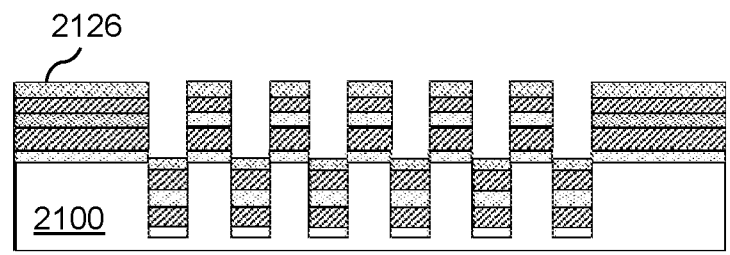

At block 2022, a protective layer 2126 (e.g., a protective chrome layer) is deposited as shown in FIG. 21O. Protective layer 2126 may have a thickness of, for example, 1 µm or less (e.g., approximately 500 nm).

Figure 21P:
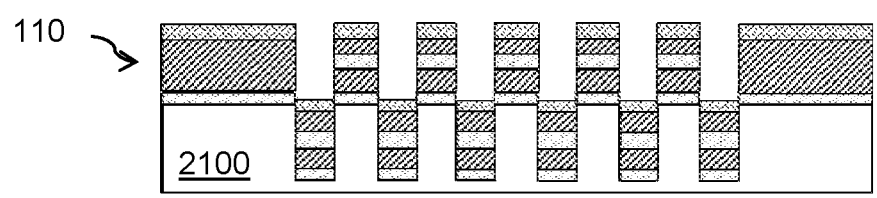

At block 2024, Nitinol layers 2110, 2124 and bonding layer 2118 are annealed to form thin-film mesh 110 as shown in FIG. 21P. Wafer 2100 with Nitinol layers 2110, 2124 and bonding layer 2114 may be annealed at a high temperature (e.g., approximately 675° C. for approximately 10 minutes) to melt bonding layer 2118 and crystalize amorphous Nitinol layers 2110, 2124. Nitinol layer 2110 and Nitinol layer 2124 are fused in inseam region 2116.

Figure 21Q:

At block 2026, thin-film mesh 110 is released as shown in FIG. 21Q. Annealed wafer 2100 may be placed in chrome etchant (e.g., for approximately 1 hour) to release thin-film mesh 110 from top of the wafer 2100.

At block 2028, thin-film mesh 110 is expanded to form a three-dimensional thin-film mesh 110 with spirals that have been opened up, such as spirals as shown in FIGS. 15B and 16B. It will be appreciated that combining the lift-off process with multiple-layer depositions of Nitinol separated by layers of sacrificial layers enables fabrication of thin-film meshes 110 of various other three-dimensional shapes in other embodiments.

A thin-film mesh membrane (e.g., thin-film mesh 110), or a corresponding hybrid membrane/structure may be used for various medical treatments as described below.

In some embodiments, a thin-film mesh membrane may be used at various treatment locations in a patient, such as in various types of neurovasculature, carotid vascular beds, cardiac vascular beds, aortic vascular beds, iliac vascular beds, renal vascular beds, peripheral vascular beds, upper extremity vascular beds, and other similar treatment locations.

In some embodiments, a thin-film mesh membrane, a thin-film mesh structure, or a corresponding hybrid membrane/structure may be used, for example, to facilitate wound healing for burns, pressure ulcers, scar revisions, ischemic lower limb ulcers, and other acute and chronic wounds.

In some embodiments, a thin-film mesh membrane, a thin-film mesh structure, or a corresponding hybrid membrane/structure may be used to stop acute bleeding whether from injury or from surgical intervention ("hemostasis").

In some embodiments, a thin-film mesh membrane, a thin-film mesh structure, or a corresponding hybrid membrane/structure may be used to facilitate bone healing that is wrapped around or placed within a fracture site, or is wrapped around structural elements formed of other materials (e.g. titanium) that bridge a gap between bones.

In some embodiments, a thin-film mesh membrane, a thin-film mesh structure, or a corresponding hybrid membrane/structure may be used to grow human chondrocytes and create a thin plate of cartilage. This cartilage plate could be used in joint operations to delay knee or hip replacement or other osteoarthritic conditions.

In some embodiments, a thin-film mesh membrane, a thin-film mesh structure, or a corresponding hybrid membrane/structure may be used to deliver chemotherapeutics directly to the site of a tumor following surgical excision of the tumor.

In some embodiments, a thin-film mesh membrane, a thin-film mesh structure, or a corresponding hybrid membrane/structure may be used in cardiac surgery to place cardiac myocytes at a site of myocardial infarction. Following infarction, the surgeon would excise the scarred area and insert the membrane or the hybrid membrane to facilitate regrowth of healthy tissue, as opposed to scar tissue that typically accompanies myocardial infarction.

In some embodiments, a thin-film mesh membrane, a thin-film mesh structure, or a corresponding hybrid membrane/structure may be used as a scaffold device for nerve regrowth following injury. The thin-film mesh membrane or hybrid membrane would have channels aligned like a native nerve to facilitate axon growth in a controlled manner.

In some embodiments, a thin-film mesh membrane, a thin-film mesh structure, or a corresponding hybrid membrane/structure may be used in reconstructive or cosmetic surgery to replace ligaments because of the elastic properties of thin-film mesh (e.g., breast tissue contains multiple small ligamentous elements that give rise to the shape and mechanical properties of the organ, and post-mastectomy prostheses, i.e., breast implants, are essentially non-structured bags of saline, silicone gel, or other materials).

In some embodiments, thin-film mesh membranes, thin-film mesh structures, and/or corresponding hybrid membranes/structures can be joined together to create the basis for more complex cartilaginous structures (e.g., external ear, portions of nose) when seeded with chondrocytes.

In some embodiments, a thin-film mesh membrane, a thin-film mesh structure, or a corresponding hybrid membrane/structure may be used to replace elements of the eye that have been injured traumatically or by disease (e.g., a tumor).

In some embodiments, a thin-film mesh membrane, a thin-film mesh structure, or a corresponding hybrid membrane/structure may be used to construct replacement elements of the bronchial tree in the lungs.

In some embodiments, a thin-film mesh membrane, a thin-film mesh structure, or a corresponding hybrid membrane/structure composed of, or including, Nitinol may be seeded with myocytes to construct replacement skeletal muscle. Because Nitinol has the ability to change shape when electrical current is passed through it, it may be advantageously be used in artificial limbs.

In some embodiments, a thin-film mesh membrane, a thin-film mesh structure, or a corresponding hybrid membrane/structure may be used as a means to deliver both small and large molecules (i.e. proteins) to anatomical sites of interest.

Where methods described above indicate certain events occurring in certain order, those of ordinary skill in the art having the benefit of this disclosure would recognize that the ordering may be modified and that such modifications are in accordance with the variations of the present disclosure. Additionally, parts of methods may be performed concurrently in a parallel process when possible, as well as performed sequentially. In addition, more steps or less steps of the methods may be performed.

Although certain illustrative embodiments and methods have been disclosed herein, it can be apparent from the foregoing disclosure to those skilled in the art that variations and modifications of such embodiments and methods can be made without departing from the true spirit and scope of this disclosure. Many other examples exist, each differing from others in matters of detail only. Accordingly, it is intended that this disclosure be limited only to the extent required by the appended claims and the rules and principles of applicable law.

What is claimed is:

1. A thin-film mesh device comprising:
a thin-film mesh that comprises a plurality of spirals interconnected to each other,
wherein the thin-film mesh comprises thin-film Nitinol (TFN).

2. The thin-film mesh device of claim 1, wherein the plurality of spirals is arranged around an approximate central point on the thin-film mesh.

3. The thin-film mesh device of claim 1, wherein each of the spirals comprises one of three spiral arms, four spiral arms, six spiral arms, twelve spiral arms, or twenty-four spiral arms.

4. The thin-film mesh device of claim 1, wherein, for each of the spirals, a distance between adjacent spiral arms increases as the spiral arms radiate out from a center of the spiral.

5. The thin-film mesh device of claim 1, wherein the thin-film mesh further comprises a plurality of triangular interconnects, wherein each of the triangular interconnects connects three of the spirals with one another.

6. The thin-film mesh device of claim 1, wherein each of the spirals is one of a logarithmic spiral, a golden spiral, an approximated golden spiral, a box Phi spiral, or a Fibonacci spiral.

7. The thin-film mesh device of claim 6, wherein each of the spirals is a box Phi spiral, which is one of a two box Phi spiral, a three box Phi spiral, or a four box Phi spiral.

8. The thin-film mesh device of claim 1, wherein the thin-film mesh is at least one of coated or conjugated to a therapeutic modality.

9. The thin-film mesh device of claim 8, wherein the therapeutic modality comprises at least one of small molecules, peptides, antibodies, polymers, biopolymers, cell, or engineered cells.

10. A thin-film mesh device comprising:
a backbone extending in a longitudinal axis; and
a thin-film mesh assembled on the backbone,
wherein the thin-film mesh comprises a plurality of spirals interconnected to each other, and wherein the thin-film mesh comprises thin-film Nitinol (TFN).

11. The thin-film mesh device of claim 10, wherein the plurality of spirals is arranged around an approximate central point on the thin-film mesh.

12. The thin-film mesh device of claim 10, wherein each of the spirals comprises one of three spiral arms, four spiral arms, six spiral arms, twelve spiral arms, or twenty-four spiral arms.

13. The thin-film mesh device of claim 10, wherein the thin-film mesh further comprises a plurality of triangular interconnects, wherein each of the triangular interconnects connects three of the spirals with one another.

14. The thin-film mesh device of claim 10, wherein the thin-film mesh comprises a cylindrical shape, and wherein at least one of the spirals is expanded such that the thin-film mesh expands along the longitudinal axis of the cylindrical shape and along a circumferential direction of the cylindrical shape.

15. The thin-film mesh device of claim 14, wherein the thin-film mesh is expandable along the circumferential direction allowing the cylindrical shape to expand radially increasing a diameter of the cylindrical shape.

16. The thin-film mesh device of claim 10, wherein the backbone comprises a plurality of S-shaped curves.

17. A thin-film mesh device comprising:
a thin-film mesh that comprises a plurality of spirals interconnected to each other,
wherein the thin-film mesh comprises a cylindrical shape, and wherein at least one of the spirals is expanded such that the thin-film mesh expands along the longitudinal axis of the cylindrical shape and along a circumferential direction of the cylindrical shape.

* * * * *